United States Patent
Li et al.

(10) Patent No.: US 11,254,766 B2
(45) Date of Patent: Feb. 22, 2022

(54) SURFACTANT RESPONSIVE EMULSION POLYMERIZED MICRO-GELS

(71) Applicant: Lubrizol Advanced Materials, Inc., Cleveland, OH (US)

(72) Inventors: Dongcui Li, North Royalton, OH (US); Shui-Jen Raymond Hsu, Foothill Ranch, CA (US); Krishnan Chari, Hudson, OH (US)

(73) Assignee: Lubrizol Advanced Materials, Inc., Cleveland, OH (US)

( * ) Notice: Subject to any disclaimer, the term of this patent is extended or adjusted under 35 U.S.C. 154(b) by 0 days.

(21) Appl. No.: 16/470,788

(22) PCT Filed: Dec. 15, 2017

(86) PCT No.: PCT/US2017/066655
§ 371 (c)(1),
(2) Date: Jun. 18, 2019

(87) PCT Pub. No.: WO2018/118679
PCT Pub. Date: Jun. 28, 2018

(65) Prior Publication Data
US 2019/0345282 A1    Nov. 14, 2019

Related U.S. Application Data

(60) Provisional application No. 62/435,968, filed on Dec. 19, 2016.

(51) Int. Cl.
| | | |
|---|---|---|
| *C08F 220/28* | (2006.01) | |
| *A61K 8/04* | (2006.01) | |
| *A61K 8/44* | (2006.01) | |
| *A61K 8/81* | (2006.01) | |
| *A61Q 19/00* | (2006.01) | |
| *C09K 8/035* | (2006.01) | |
| *C09K 8/62* | (2006.01) | |

(52) U.S. Cl.
CPC ............ *C08F 220/28* (2013.01); *A61K 8/042* (2013.01); *A61K 8/442* (2013.01); *A61K 8/8152* (2013.01); *A61Q 19/00* (2013.01); *C09K 8/035* (2013.01); *C09K 8/62* (2013.01); *A61K 2800/26* (2013.01); *A61K 2800/48* (2013.01); *A61K 2800/548* (2013.01); *A61K 2800/5422* (2013.01); *C08F 220/281* (2020.02); *C08F 2400/00* (2013.01)

(58) Field of Classification Search
CPC .. C08F 220/28; C08F 220/20; C08F 2400/00; C08F 2/30
USPC ........................................ 424/401; 514/772.5
See application file for complete search history.

(56) References Cited

U.S. PATENT DOCUMENTS

2014/0114006 A1* 4/2014 Palmer, Jr. ................ C08F 2/30
                                                          524/458
2014/0341957 A1* 11/2014 Yang ........................ C09K 8/68
                                                          424/401

FOREIGN PATENT DOCUMENTS

| WO | 2011/068820 A1 | 6/2011 |
| WO | 2015/095286 A1 | 6/2015 |
| WO | 2016/033012 A1 | 3/2016 |
| WO | 2016/100183 A1 | 6/2016 |

* cited by examiner

*Primary Examiner* — Tri V Nguyen
(74) *Attorney, Agent, or Firm* — Thoburn Dunlap

(57) ABSTRACT

A crosslinked, nonionic, amphiphilic polymer is prepared by polymerizing a monomer mixture comprising an amphiphilic additive. The obtained polymer is useful for forming a clearer yield stress fluid in combination with a surfactant. The yield stress fluid is capable of suspending insoluble materials in the presence of electrolytes, perfumes, fragrances and/or organic acid preservatives.

30 Claims, 3 Drawing Sheets

SURFACTANT RESPONSIVE EMULSION POLYMERIZED MICRO-GELS

CROSS REFERENCE TO RELATED APPLICATION

This application claims priority from PCT Application Serial No. PCT/US2017/066655 filed on Dec. 15, 2017, which claims the benefit of U.S. Provisional Application No. 62/435,968 filed on Dec. 19, 2016, both of which are incorporated in their entirety by reference herein.

FIELD OF THE DISCLOSED TECHNOLOGY

The disclosed technology relates to rheology modifiers and more specifically to a yield stress fluid comprising a surfactant responsive micro-gel. The disclosed technology also relates to the formation of a rheologically and phase stable surfactant responsive micro-gel composition with improved clarity. Additionally, the disclosed technology relates to the formation of a clear, rheologically and phase stable surfactant responsive micro-gel composition that can be used over a broad pH range to suspend particulates, insoluble materials, perfumes and fragrances in the presence of electrolytes and/or low pH organic acid preservatives.

BACKGROUND OF THE DISCLOSED TECHNOLOGY

We are surrounded in everyday life by yield stress fluids. Simply stated, yield stress fluids remain stationary until a sufficient stress is placed on the fluid at which point the fluid will flow. It can be thought of as the initial resistance to flow under stress and is also referred to as yield value. Yield stress is a measurable quantity similar to, but not dependent on viscosity. While a certain rheology modifier may thicken or enhance the viscosity of a composition in which it is included, it does not necessarily have desirable yield stress properties.

A desirable yield stress property is critical to achieving certain physical and aesthetic characteristics in a liquid medium, such as the indefinite suspension of particles, insoluble liquid droplets, or the stabilization of gas bubbles within a liquid medium. Particles dispersed in a liquid medium will remain suspended if the yield stress (yield value) of the medium is sufficient to overcome the effect of gravity or buoyancy on those particles. Insoluble liquid droplets can be prevented from rising and coalescing and gas bubbles can be suspended and uniformly distributed in a liquid medium using yield value as a formulating tool. An example of a yield stress fluid is a micro-gel rheology modifier which is used generally to adjust or modify the rheological properties of aqueous compositions. Such properties include, without limitation, viscosity, flow rate, stability to viscosity change over time, and the ability to suspend particles for indefinite periods of time. They are useful in a number of consumer and industrial applications. An important consumer application includes their use in the formulation of personal care products such as body washes, skin creams, toothpastes, shampoos, hair gels and other cosmetics. In industrial applications, they are useful as subterranean treatment fluids in the oil and gas industry as a component in drilling and fracturing fluids. Typically, they comprise chemically crosslinked polymers having a pH-responsive functionality that is either base or acid sensitive. The polymers may be mixed with other ingredients in a formulation and then neutralized by the addition of a neutralization agent such as an acid or a base. Acid sensitive thickeners are activated upon contact with an acidic agent, while base-sensitive thickeners are activated upon contact with an alkaline agent. Upon neutralization, the polymers swell significantly to form a randomly close-packed (RCP) jammed network of swollen cross-linked micro-gel particles imparting a desired rheological profile, i.e., yield stress, elastic modulus, and viscosity, as well as optical clarity to the formulation.

These types of rheology modifiers are well known in the art. For example, U.S. Pat. Nos. 2,798,053; 2,858,281; 3,032,538; and 4,758,641 describe cross-linked carboxylic acid polymers based on acrylic acid, maleic acid, itaconic acid or methacrylic acid monomers. U.S. Pat. No. 6,635,702 describes crosslinked alkali-swellable acrylate copolymers comprising one or more carboxylic acid monomers and one or more non-acid vinyl monomers. U.S. Pat. No. 7,378,479 discloses a crosslinked acid-swellable polymer containing at least one basic amino substituent that is cationic at low pH, at least one hydrophobically modified polyoxyalkylene substituent derived from an associative vinyl monomer, and at least one polyoxyalkylene substituent derived from a semi-hydrophobic vinyl surfactant monomer. A key feature of these pH-responsive micro-gels is the very large increase in diameter (or size) of individual cross-linked polymer particles upon neutralization. The high swelling efficiency allows formulators to achieve the desired yield stress and viscosity using relatively small amounts of polymer resulting in low cost-in-use. Dalmont, Pinprayoon and Saunders (*Langmuir* vol. 24, page 2834, 2008) show that individual particles in a micro-gel dispersion of a copolymer of ethyl acrylate, and methacrylic acid cross-linked with butanediol diacrylate increase in diameter by at least a factor of 3 upon pH-activation or neutralization. The level of swelling causes an increase in volume fraction of at least 27 ($3^3$). A jammed network is achieved upon neutralization (or activation) with a relatively low concentration of polymer (less than 3 wt. %).

Although pH-responsive micro-gels provide yield stress fluids with the high efficiency that is desired by the formulator, they suffer from a major disadvantage in that their thickening ability is greatly reduced by the presence of moderate amounts of electrolytes such as sodium chloride, calcium chloride and magnesium sulfate in the medium. They do not effectively maintain their viscosity and drastic viscosity losses in the presence of inorganic electrolytes are observed. Moreover, rheological properties are not uniform across a broad range in pH and show sharp changes as a function of pH. Additionally, the commercial product formulator utilizing these pH responsive thickeners must design the manufacturing process to account for the necessary neutralization step which is not always compatible with the other formulation steps and/or ingredients needed in the process. To overcome these difficulties, various non-ionic thickeners have been proposed. U.S. Pat. No. 4,722,962 describes non-ionic associative thickeners comprising a water-soluble monoethylenically unsaturated monomer and a non-ionic urethane monomer. These polymers provide increases in viscosity or thickening of aqueous formulations that is relatively independent of pH but the polymers are not cross-linked and the purely associative interactions do not create a yield stress.

In addition to pH-responsive micro-gels, temperature-responsive micro-gels are known in the art. Senff and Richtering (*Journal of Chemical Physics*, vol. 111, page 1705, 1999) describe the change in size of non-ionic chemically cross-linked poly (N-isopropylacrylamide) (PNIPAM)

micro-gel particles as a function of temperature. The particles swell by almost a factor of 2.5 in diameter (15 times in terms of volume fraction) when the temperature is reduced from 35° C. to 10° C. Although this represents a significant degree of swelling, the use of temperature to activate micro-gels is undesirable. A method of activation is needed that enables switching from a free-flowing suspension to a jammed yield stress fluid under ambient conditions.

Wu and Zhou (*Journal of Polymer Science*: Part B: Polymer Physics, vol. 34, page 1597, 1996) describe the effect of surfactant on swelling of chemically cross-linked PNIPAM homo-polymer micro-gel particles in water. The use of surfactants to activate micro-gels is attractive because many formulations contain surfactants as co-ingredients. However, the efficiency of swelling reported by Wu and Zhou is extremely low. The anionic surfactant sodium dodecyl (lauryl) sulfate increases the size of cross-linked PNIPAM particles by only a factor of 1.4 at room temperature. Furthermore, Wu and Zhou do not teach how to create a shear thinning yield stress fluid with high optical clarity.

Hidi, Napper and Sangster (*Macromolecules*, vol. 28, page 6042, 1995) describe the effect of surfactant on swelling of poly (vinyl acetate) homopolymer micro-gels in water. For micro-gels that are not cross-linked they report an increase in diameter by a factor of 3 to 4 corresponding to a 30 to 60 fold change in volume of the original particles in the presence of sodium dodecyl (lauryl) sulfate. However, swelling is drastically reduced for cross-linked particles. In this case, they observe an increase in diameter by only a factor of 1.4. Once again, Hidi, Napper and Sangster do not teach how to create a shear thinning yield stress fluid with high optical clarity.

Apart from providing the necessary rheology profiles, the suspension of solids and/or insoluble materials in a phase stable system is equally important to a rheology modifier. In drilling for oil and gas, subterranean treatment fluids (e.g., drilling and fracture fluids) are typically modified with gelling agents to provide desired rheological properties. Gelling agents include any substance that is capable of increasing the viscosity of a fluid, for example, by forming a micro-gel. These agents must not only possess desirable rheological properties in terms of fluid flow and pumpability, but must also have the capability to suspend solids under both dynamic and static conditions. During active drilling operations, the drilling fluid must possess sufficient structure to carry the formation cuttings to the surface and also have the necessary shear thinning properties to be pumpable. During non-drilling periods, the drilling fluid may remain stationary in the bore hole for hours or even days at a time. During this period, settling of entrained solids can be problematic if the fluid does not have enough structure to support both large and small particulate matter.

Fracturing is used to boost the production of hydrocarbons such as petroleum or natural gas from subterranean formations. In this process, a fracturing fluid containing a gelling agent is injected through a wellbore and forced against the formation strata by high pressure sufficient to cause the strata to crack and fracture thereby liberating the hydrocarbon trapped in the formation. The fracturing fluid also carries a proppant to the fracture site. Proppant particles remain in the fracture thereby "propping" the fracture open when the well is in production. The proppant material is typically selected from sand, sintered bauxite, glass balls, polystyrene beads and the like. Whereas sufficient rheological properties are important in treatment fluids used in fracturing, satisfactory suspending ability is necessary for the transport of the proppant materials to the fracture site within the formation.

Conditions are harsh within a subterranean formation and a gelling agent must be stable to variations in temperature, brackish environments, wide ranges of pH, and changes in shear forces.

Various problems have been encountered with subterranean treatment fluids in oil field applications, including the lack of thermal stability of the gel upon exposure to varying temperatures, pH and brackish environments, as well as high shear conditions. This can result in changes in the rheological properties of the gel which can ultimately affect the ability of the fluid to suspend bore hole cuttings and or proppant materials. If particulate materials are prematurely lost from the treatment fluid, it can have a detrimental effect on the drilling and development of the formation. Furthermore, gel instability can result in higher loss of fluid into the formation thereby diminishing the efficiency of the operation.

Personal and homecare compositions which can suspend particles and/or other water insoluble materials are very desirable. These materials impart or contribute to a variety of user benefits including but not limited to exfoliation, visual aesthetics, and/or the encapsulation and release of beneficial agents upon use. The suspension of particulate and insoluble materials as active and aesthetic agents in personal and homecare compositions is becoming increasingly popular with formulators. Typically, particles are suspended in these compositions using structuring systems such as acrylate polymers, structuring gums (e.g., xanthan gum), starch, agar, hydroxyl alkyl cellulose, etc. However, the addition of beads or particles to personal care compositions tends to be problematic. For example, one problem is that particles or insoluble materials very frequently tend to be of a different density than the continuous phase of the composition to which they are added. This mismatch in the density can lead to separation of the particles from the continuous phase and a lack of overall product stability. In one aspect, when added particles are less dense than that of the composition continuous phase, the particles tend to rise to the top of such phase ("creaming"). In another aspect, when the added particles have a density greater than that of the continuous phase, the particles tend to gravitate to the bottom of such phase ("settling"). When large particles are desired to be suspended (e.g., polyethylene particles, guar beads, etc.), the level of polymer used is typically increased to provide increased structure for suspended beads. A consequence of thickening a liquid to provide structure for suspended beads causes a significant increase in liquid viscosity and a corresponding decrease in pourability, a property which is not always desirable. Highly viscous products are typically difficult to apply and rinse away, especially if the shear thinning profile of the viscosity building agent is deficient. High viscosities can also adversely affect packaging, dispensing, dissolution, and the foaming and sensory properties of the product. Moreover, conventionally structured liquids are often opaque or turbid thereby obscuring the suspended beads from the consumer, which adversely affects the aesthetic appeal of the product.

Many common thickeners such as xanthan gum, carboxymethylcellulose (CMC), carrageenan, and acrylic acid homopolymers and copolymers are anionic and therefore, can react with the cationic surfactants and cause precipitation of the cationic and thickener or reduce the efficacy of the cationic surfactant. Non-ionic thickeners such as hydroxyethylcellulose (HEC) and hydroxypropylmethylcellulose (HPMC) can provide viscosity in cationic systems, however, very little suspension properties are imparted to the fluid. Cationic thickeners such as Polyquaternium-10 (cationically modified HEC) and cationic guar provide thickening in cationic systems but not suspension. Some acrylic polymers are effective at thickening cationic systems but they can be limited by pH, require high concentrations, have high cost-in-use, and often have narrow limits of compatibility with the cationic materials.

Anionic surfactants are often used as detersive agents in cleansers and cleaning products because of their excellent cleaning and foaming properties. Exemplary anionic surfactants traditionally utilized in these formulations include, for example, alkyl sulfates and alkyl benzene sulfonates. While the anionic surfactants and, in particular, the anionic sulfates and sulfonates are efficient detersive agents, they are severe ocular irritants and capable of causing mild to moderate dermal irritation to some sensitized persons. Accordingly, it has become increasingly important to consumers that aqueous cleansing compositions be mild in that they do not irritate the eyes and skin when in use. Manufacturers are striving to provide mild cleansing products that also incorporate insoluble benefit and/or aesthetic agents that require stable suspension. It is known that the irritation caused by anionic sulfates and sulfonates can be reduced by utilizing the ethoxylated forms thereof. While ethoxylated surfactants may mitigate ocular and skin irritation in compositions in which they are included, a major problem in using these surfactants is that it is difficult to obtain desirable yield stress properties in an ethoxylated system.

One important class of liquid rheology modifier commonly employed to thicken aqueous based surfactant containing formulations is the alkali-swellable or alkali-soluble emulsion (ASE) polymers. ASE polymers are linear or crosslinked copolymers that are synthesized from (meth) acrylic acid and alkyl acrylates. The crosslinked polymers immediately thicken upon neutralization with an inorganic or an organic base. As liquid emulsions, ASE polymers are easily processed and formulated into liquid surfactant containing formulations by the product formulator. Examples of ASE polymer thickened surfactant based formulations are set forth in U.S. Pat. No. 6,635,702; International Published Application No. WO 01/19946; and European Patent No. 1 690 878 B1, which disclose the use of a polymeric thickener for aqueous compositions containing surfactants. Although these thickeners offer good viscosity, suspension and clarity properties in surfactant containing formulations at pH values near neutral (pH 6.0), they become hazy at acidic pH ranges, resulting in poor clarity.

Microbial contamination from bacteria, yeast, and/or fungus in cosmetics, toiletries, and personal and homecare products is very common and has been of great concern to the industry for many years. Present day surfactant containing products are typically formulated with a preservative to protect the product from decay, discoloration, or spoilage and to ensure that the product is safe for topical application to hard surface substrates and laundry items in homecare applications, and to the skin, scalp, and hair in humans and animals in personal and animal care applications. Three classes of preservative compounds that are commonly used in surfactant containing products are the formaldehyde donors such as diazolinyl urea, imidazolinyl urea, and DMDM Hydantoin; the halogenated compounds including 2,4-dichlorobenzyl-alcohol, Chloroxylenol (4-chloro-3,5-dimethyl-phenol), Bronopol (2-bromo-2-nitropropane-1,3-diol), and iodopropynyl butyl carbamate; and the paraben compounds including methyl-paraben, ethyl-paraben, propyl-paraben, butyl-paraben, isopropyl-paraben, and benzyl-paraben.

While these preservatives have been successfully utilized in personal care products for many years, there are recent concerns by the scientific community and the public that some of these compounds may constitute health hazards. Accordingly, there is an interest in replacing the above-mentioned compounds in surfactant containing products that are topically applied to or come into contact with human skin, scalp or hair while maintaining good antimicrobial efficacy, mildness, and do not raise safety concerns.

Organic acids (e.g., sorbic, citric and benzoic), such as those used as preservatives in the food industry, have been increasingly looked at as the ideal replacement for the foregoing preservative systems in surfactant containing formulations. The antimicrobial activity of the organic acids is connected to the associated or protonated species of the acid molecule. As the pH of an organic acid containing formulation increases, dissociation of the proton occurs forming acid salts. The dissociated form of the organic acids (acid salts) have no antimicrobial activity when used alone, effectively limiting the use of organic based acids to pH values below 6 (Weber, K. 2005. New alternatives to paraben-based preservative blends. *Cosmetics & Toiletries* 120(1): 57-62).

The literature has also suggested that formulating products in the natural pH range (between about 3-5) 1) reduces the amount of preservative required in a product by enhancing preservative efficacy, 2) stabilizes and increases the effectiveness of many cosmetic active ingredients, 3) is beneficial to the repair and maintenance of skin barrier tissue, and 4) supports the natural skin flora to the exclusion of over-colonization by deleterious microorganisms (Wiechers, J. W. 2008. Formulating at pH 4-5: How lower pH benefits the skin and formulations. *Cosmetics & Toiletries* 123(12): 61-70).

U.S. Pat. No. 5,139,770 describes the use of crosslinked homopolymers of vinyl pyrrolidone in surfactant containing formulations such as conditioning shampoo to obtain relatively high viscosities. However, the patent does not teach how to create a yield stress fluid with high optical clarity that is also shear thinning.

As the industry desires new thickened surfactant based products that are formulated in the acidic pH range, there is a developing need for a rheology modifier that, when used in combination with a surfactant, provides a high clarity formulation under acidic pH conditions while maintaining a good viscosity/rheology profile, suspension (yield value), and enhanced aesthetics.

U.S. Pat. No. 5,663,258 describes the preparation of crosslinked copolymers of vinyl pyrrolidone/vinyl acetate. High viscosities are obtained when the polymer is combined with water but there is no teaching about using the polymer to create a yield stress fluid that is activated by surfactant.

U.S. Pat. No. 6,645,476 discloses a water soluble polymer prepared from the free radical polymerization of a hydrophobically modified ethoxylated macromer in combination with a copolymerizable second monomer selected from unsaturated acids and their salts and/or a myriad of other monomers including N-vinyl lactams and vinyl acetate. Preferred polymers are crosslinked and are polymerized from hydrophobically modified ethoxylated macromers in combination with neutralized 2-acrylamido-2-methylpropane sulfonic acid. The viscosities of 1% aqueous solutions of the polymer preferably range from 20,000 mPa·s to 100,000 mPa·s. There is no teaching of a surfactant activated polymer devoid of hydrophobically modified ethoxylated macromer repeating units providing a yield stress fluid exhibiting good suspension properties without a substantial increase in viscosity.

International Publication Nos. WO 2015/095286 and WO 2016/100183 describe a surfactant activated nonionic amphiphilic polymer crosslinked with an amphiphilic crosslinking agent. These polymers not only demonstrate the ability to effectively suspend particles and/or insoluble materials within surfactant containing compositions, but also exhibit desirable mildness, desirable rheology profiles, clarity and aesthetic characteristics across a wide range of temperature, pH conditions and electrolyte concentrations at low polymer usage levels. The yield stress, elastic modulus and optical clarity are substantially independent of pH.

SUMMARY OF THE DISCLOSED TECHNOLOGY

The present technology provides crosslinked, nonionic, amphiphilic polymers (amphiphilic polymers for brevity) that can be swollen in the presence of a surfactant. Surfactant compositions comprising these amphiphilic polymers are substantially clearer and less turbid than the surfactant compositions containing the polymers described in WO 2015/095286 and WO 2016/100183. The amphiphilic polymers of the present technology are prepared by the emulsion polymerization of a monomer mixture comprising at least one monomer selected from a $C_1$ to $C_5$ hydroxyalkyl (meth)acrylate, at least one monomer selected from a $C_1$ to $C_5$ alkyl (meth)acrylate, at least one monomer selected from an associative monomer, a semi-hydrophobic monomer and mixtures thereof and an amphiphilic crosslinking monomer. The crosslinking monomer is an amphiphilic crosslinking agent, or a mixture of an amphiphilic crosslinking agent and a conventional crosslinking agent. Surprisingly, the rheological profiles of aqueous surfactant systems containing these amphiphilic polymers are maintained and the clarity of these surfactant systems are improved when the polymerizable monomer mixture used to prepare the amphiphilic polymer includes an amphiphilic additive. Clarity is improved in the presence of electrolytes such as inorganic salts, acid preservatives and perfumes and fragrances.

In one aspect, the disclosed technology relates to a yield stress fluid comprising a crosslinked, nonionic, amphiphilic emulsion polymer and a surfactant wherein the amphiphilic emulsion polymer is prepared in the presence of an amphiphilic additive.

In one aspect, the disclosed technology relates to a crosslinked, nonionic, amphiphilic emulsion polymer and a surfactant wherein the amphiphilic emulsion polymer is prepared in the presence of an amphiphilic additive and in the absence of protective colloid or polymeric stabilizer.

In one aspect, the disclosed technology relates to a crosslinked, nonionic, amphiphilic emulsion polymer and a surfactant wherein the amphiphilic emulsion polymer is prepared in the presence of an amphiphilic additive and in the absence of poly(vinyl alcohol) or partially hydrolyzed poly(vinyl acetate).

In another aspect, the disclosed technology relates to a thickened aqueous composition with improved clarity properties comprising a crosslinked, nonionic, amphiphilic emulsion polymer and at least one surfactant, wherein the amphiphilic emulsion polymer is prepared from a monomer mixture containing an amphiphilic additive, and the concentration of the amphiphilic emulsion polymer is no more than 5 wt. % based on the total weight of the composition, and the at least one surfactant is no more than 70 wt. % of the composition, and the yield stress of the composition is at least 1 mPa, or 0.1 Pa with a shear thinning index of less than 0.5 at shear rates between about 0.1 and about 1 reciprocal seconds, and wherein the yield stress, elastic modulus and optical clarity of the composition are substantially independent of pH in the range of about 2 to about 14.

In still another aspect, an embodiment of the disclosed technology relates to a thickened aqueous composition comprising a crosslinked, nonionic, amphiphilic polymer and at least one surfactant, wherein the amphiphilic emulsion polymer is prepared from a monomer mixture containing an amphiphilic additive, and wherein the concentration of the amphiphilic emulsion polymer is no more than 5 wt. % based on the total weight of the composition, and the at least one surfactant is no more than 70 wt. % of the composition, wherein the ratio of the standard deviation to the mean of measured values for yield stress, elastic modulus and optical clarity is less than 0.3 in one aspect, and less than 0.2 in another aspect in the pH range from about 2 to about 14.

In still another aspect, an embodiment of the disclosed technology relates to a thickened aqueous composition comprising a crosslinked, nonionic, amphiphilic polymer and at least one surfactant, wherein the amphiphilic emulsion polymer is prepared from a monomer mixture containing an amphiphilic additive, and wherein the concentration of the polymer is no more than 5 wt. % based on the total weight of the composition, and at least one surfactant is no more than 70 wt. % of the composition, the yield stress of the composition is at least 1 mPa, or 0.1 Pa with a shear thinning index of less than 0.5 at shear rates between about 0.1 and about 1 reciprocal seconds, and wherein the yield stress, elastic modulus and optical clarity of the composition are substantially independent of pH in the range of about 2 to about 14 and wherein the composition is able to suspend beads of a size between 0.5 and 1.5 mm wherein the difference in specific gravity of the beads relative to water is in the range of 0.2 to 0.5 for a period of at least 4 weeks at room temperature.

In still another aspect, an embodiment of the disclosed technology relates to a thickened aqueous composition comprising a crosslinked, nonionic, amphiphilic polymer and one or more surfactants, wherein the amphiphilic emulsion polymer is prepared from a monomer mixture containing an amphiphilic additive, wherein the concentration of the polymer is no more than 5 wt. % based on the total weight of the composition, wherein the total concentration of surfactant is no more than 70 wt. % of the composition, the yield stress of the composition is at least 1 mPa, or 0.1 Pa with a shear thinning index of less than 0.5 at shear rates between about 0.1 and about 1 reciprocal seconds, and wherein the yield stress, elastic modulus and optical clarity of the composition are substantially independent of pH in the range of about 2 to about 14 and wherein the composition is able to suspend beads of a size between 0.5 and 1.5 mm where the difference in specific gravity of the beads relative to water is in the range of 0.2 to 0.5 for a period of at least 4 weeks at room temperature and wherein one of the surfactants contains ethylene oxide moieties and said surfactant is more than 75% by weight of the total surfactant.

In still another aspect, an embodiment of the disclosed technology relates to a thickened aqueous composition comprising a crosslinked, nonionic, amphiphilic polymer and at least one surfactant, wherein the amphiphilic emulsion polymer is prepared from a monomer mixture containing an amphiphilic additive, wherein the concentration of the polymer is no more than 5 wt. % based on the total weight of the composition, and the at least one surfactant is no more than 70 wt. % of the composition, the yield stress of the composition is at least 1 mPa, or 0.1 Pa with a shear thinning index of less than 0.5 at shear rates between about 0.1 and about 1 reciprocal seconds, and wherein the viscosity, yield stress, elastic modulus and optical clarity of the composition are substantially independent of pH in the range of about 2 to about 14, and wherein the rheology profiles such as viscosity and yield stress is synergistically enhanced in the presence of an electrolyte such as an inorganic salt.

In still another aspect, an embodiment of the disclosed technology relates to a thickened aqueous composition comprising a crosslinked, nonionic, amphiphilic polymer and at least one surfactant, wherein the amphiphilic emulsion polymer is prepared from a monomer mixture containing an amphiphilic additive, wherein the concentration of the polymer is no more than 5 wt. % based on the total weight of the composition, and the at least one surfactant is no more than 70 wt. % of the composition, the yield stress of the composition is at least 1 mPa, or 0.1 Pa with a shear thinning index of less than 0.5 at shear rates between about 0.1 and about 1 reciprocal seconds, and wherein the viscosity, yield stress, elastic modulus and optical clarity of the composition are maintained in the presence of a low pH organic acid preservative.

The crosslinked, nonionic, amphiphilic polymer compositions as well as the thickened aqueous fluid comprising the nonionic, amphiphilic, polymer compositions and the at least one surfactant of the disclosed technology may suitably comprise, consist of, or consist essentially of the components, elements, and process delineations described herein. The disclosed technology illustratively disclosed herein suitably may be practiced in the absence of any element which is not specifically disclosed herein.

Unless otherwise stated, all percentages, parts, and ratios expressed herein are based upon the total weight of the components contained in the compositions of the disclosed technology.

As used herein, the term "amphiphilic polymer" means that the polymeric material has distinct hydrophilic and hydrophobic portions. "Hydrophilic" typically means a portion that interacts intramolecularly with water and other polar molecules. "Hydrophobic" typically means a portion that interacts preferentially with oils, fats or other non-polar molecules rather than aqueous media.

As used herein, the term "hydrophilic monomer" means a monomer that is substantially water soluble. "Substantially water soluble" refers to a material that is soluble in distilled (or equivalent) water, at 25° C., at a concentration of about 3.5% by weight in one aspect, and soluble at about 10% by weight in another aspect (calculated on a water plus monomer weight basis).

As used herein, the term "hydrophobic monomer" means a monomer that is substantially water insoluble. "Substantially water insoluble" refers to a material that is not soluble in distilled (or equivalent) water, at 25° C., at a concentration of about 3% by weight in one aspect, and not soluble at about 2.5% by weight in another aspect (calculated on a water plus monomer weight basis).

The term "nonionic" as used herein encompasses both a monomer, monomer composition or a polymer polymerized from a monomer composition devoid of ionic or ionizable moieties ("nonionizable"), and a "substantially nonionic" monomer, monomer composition or polymer polymerized from a monomer composition.

An ionizable moiety is any group that can be made ionic by neutralization with an acid or a base.

An ionic or an ionized moiety is any moiety that has been neutralized by an acid or a base.

By "substantially nonionic" is meant that the monomer, monomer composition or polymer polymerized from a monomer composition contains less than or equal to 15 wt. % in one aspect, less than or equal to 10 wt. % in another aspect, less than or equal to 5 wt. % in still another aspect, less than or equal to 3 wt. % in a further aspect, less than or equal to 1 wt. % in a still further aspect, less than or equal to 0.5 wt. % in an additional aspect, less than or equal to 0.1 wt. % in a still additional aspect, and less than or equal to 0.05 wt. % in a further aspect, of an ionizable and/or an ionized moiety. Those of ordinary skill in the art will recognize that depending on the commercial source, some nonionic monomers may contain residual amounts of a monomer with ionic or ionizable character. The amount of residual monomer in a nonionic monomer composition that contains ionic or ionizable moieties can range from 0, 0.05, 0.5, 1, 2, 3, 4, or 5 to 15 wt. % based on the weight of the particular nonionic monomer.

For the purpose of the specification the prefix "(meth) acryl" includes "acryl" as well as "methacryl". For example, the term "(meth)acrylate" includes both acrylate and methacrylate.

DESCRIPTION OF EXEMPLARY EMBODIMENTS

Figure 1:
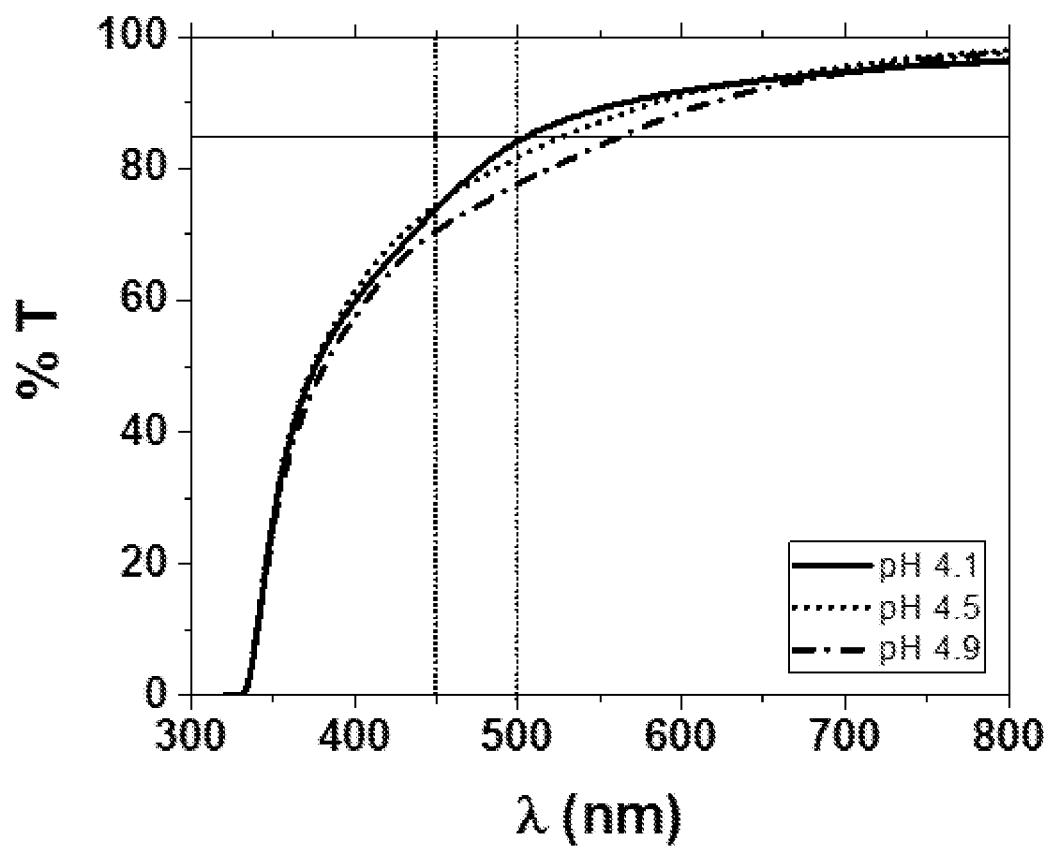
FIG. 1 is a light transmittance curve (% T versus the wavelength of visible light) of surfactant formulations formulated at various pH values containing the crosslinked, nonionic, amphiphilic polymer of Comparative Example 1.

Exemplary embodiments in accordance with the disclosed technology will be described. Various modifications, adaptations or variations of the exemplary embodiments described herein may become apparent to those skilled in the art as such are disclosed. It will be understood that all such modifications, adaptations or variations that rely upon the teachings of the disclosed technology, and through which these teachings have advanced the art, are considered to be within the scope and spirit of the disclosed technology.

While overlapping weight ranges for the various components and ingredients that can be contained in the compositions of the disclosed technology have been expressed for selected embodiments and aspects of the disclosed technology, it should be readily apparent that the specific amount of each component in the disclosed compositions and polymer components will be selected from its disclosed range such that the amount of each component is adjusted so the sum of all components in the composition or polymer component will total 100 weight percent. The amounts employed will vary with the purpose and character of the desired product and can be readily determined by one skilled in the art.

Unexpectedly, it has been discovered that highly efficient yield stress fluids with excellent shear thinning and optical clarity over a broad pH range are obtained if certain chemically crosslinked, nonionic (or substantially nonionic), amphiphilic emulsion polymers are mixed with surfactants in water. It has been determined that crosslinking with an amphiphilic crosslinker and the addition of an amphiphilic additive to the polymerizable monomer mixture before polymerization commences provides a polymer with the right balance between mechanical rigidity of the particles and expansion in aqueous surfactant media, as well as improved clarity properties of surfactant compositions in which they are contained. The crosslinked, nonionic (or substantially nonionic), amphiphilic polymers of the present technology display high surfactant activated swelling in water with increases in particle diameter of at least a factor of 2.5 in one aspect and at least 2.7 in another aspect. Furthermore, swollen micro-gels based on the polymers of the disclosed technology interact with each other in aqueous surfactant media to create soft glassy materials (SGMs) with high yield stress and shear thinning flow that is substantially independent of pH. Moreover, it has been unexpectedly found that the polymers not only maintain the rheological profiles (e.g., viscosity and yield value) of aqueous surfactant systems in which they are included, but also improve the clarity and turbidity properties of such compositions.

Amphiphilic Polymer

In one aspect of the disclosed technology, the crosslinked, nonionic, amphiphilic polymers are polymerized from monomer components that contain free radically polymerizable monounsaturation. In one embodiment, the crosslinked, nonionic, amphiphilic polymers useful in the practice of the disclosed technology are prepared from a monomer mixture comprising: a) at least one monomer selected from a $C_1$ to $C_5$ hydroxyalkyl (meth)acrylate; b) at least one monomer selected from a $C_1$ to $C_5$ alkyl (meth)acrylate; c) at least one monomer selected from an associative monomer, a semi-hydrophobic monomer and mixtures thereof; d) at least one polyunsaturated amphiphilic crosslinking monomer; and e) an amphiphilic additive, wherein the polymerizable monomer mixture containing the amphiphilic additive is free of a protective colloid and/or a polymeric stabilizer. In one embodiment, the monomer mixture is polymerized in a medium devoid of protective colloids and/or polymeric steric stabilizers.

In one embodiment, the crosslinked, nonionic, amphiphilic polymers useful in the practice of the disclosed technology are prepared from a monomer mixture comprising: a) at least one monomer selected from 2-hydroxyethyl methacrylate; b) at least one monomer selected from a ethyl acrylate, butyl acrylate, and mixtures thereof: c) at least one monomer selected from cetearyl polyethoxylated methacrylate, behenyl polyethoxylated methacrylate, and mixtures thereof; d) an amphiphilic crosslinking monomer; and e) an amphiphilic additive, wherein said polymerizable monomer mixture containing the amphiphilic additive is free of a protective colloid and/or a polymeric stabilizer. In one embodiment, the monomer mixture is polymerized in a medium devoid of protective colloids and/or polymeric steric stabilizers.

The hydroxy($C_1$-$C_5$)alkyl (meth)acrylates can be structurally represented by the following formula:

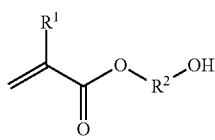

wherein $R^1$ is hydrogen or methyl and $R^2$ is an divalent alkylene moiety containing 1 to 5 carbon atoms, wherein the alkylene moiety optionally can be substituted by one or more methyl groups. Representative monomers include 2-hydroxyethyl(meth)acrylate, 3-hydroxypropyl(meth)acrylate, 4-hydroxybutyl(meth)acrylate, and mixtures thereof.

The ($C_1$-$C_5$) alkyl (meth)acrylates can be structurally represented by the following formula:

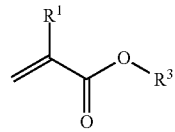

wherein $R^1$ is hydrogen or methyl and $R^3$ is $C_1$ to $C_5$ alkyl. Representative monomers include but are not limited to methyl (meth)acrylate, ethyl (meth)acrylate, butyl (meth)acrylate, sec-butyl (meth)acrylate, and iso-butyl (meth)acrylate, and mixtures thereof.

In one aspect of the disclosed technology, the polymerizable monomer mixture optionally contains a long chain alkyl (meth)acrylate represented by the formula:

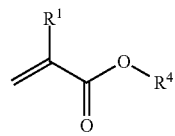

wherein $R^1$ is hydrogen or methyl and $R^4$ is $C_6$ to $C_{22}$ alkyl. Representative monomers under formula (IV) include but are not limited to hexyl (meth)acrylate, heptyl (meth)acrylate, octyl (meth)acrylate, 2-ethylhexyl (meth)acrylate, decyl (meth)acrylate, isodecyl (meth)acrylate, lauryl (meth)acrylate, tetradecyl (meth)acrylate, hexadecyl (meth)acrylate, stearyl (meth)acrylate, behenyl (meth)acrylate, and mixtures thereof.

The amount of long chain alkyl (meth)acrylate that is utilized in the polymerizable monomer mixture ranges from about 0 or 1 to about 15 wt. % in one aspect, from about 2 to about 10 wt. % in another aspect, and from about 3 to about 6 wt. % in another aspect, based on the total weight of the polymerizable monounsaturated monomers in the mixture.

The associative monomer of the disclosed technology has an ethylenically unsaturated end group portion (i) for addition polymerization with the other monomers of the disclosed technology; a polyoxyalkylene mid-section portion (ii) for imparting selective hydrophilic and/or hydrophobic properties to the product polymer, and a hydrophobic end group portion (iii) for providing selective hydrophobic properties to the polymer.

The portion (i) supplying the ethylenically unsaturated end group can be a residue derived from an α,β-ethylenically unsaturated monocarboxylic acid. Alternatively, portion (i) of the associative monomer can be a residue derived from an allyl ether or vinyl ether; a nonionic vinyl-substituted urethane monomer, such as disclosed in U.S. Reissue Pat. No. 33,156 or U.S. Pat. No. 5,294,692; or a vinyl-substituted urea reaction product, such as disclosed in U.S. Pat. No. 5,011,978; the relevant disclosures of each are incorporated herein by reference.

The mid-section portion (ii) is a polyoxyalkylene segment of about 2 to about 150 in one aspect, from about 10 to about 120 in another aspect, and from about 15 to about 60 in a further aspect of repeating $C_2$-$C_4$ alkylene oxide units. The mid-section portion (ii) includes polyoxyethylene, polyoxypropylene, and polyoxybutylene segments, and combinations thereof comprising from about 2 to about 150 in one aspect, from about 5 to about 120 in another aspect, and from about 10 to about 60 in a further aspect of ethylene, propylene and/or butylene oxide units, arranged in random or block sequences of ethylene oxide, propylene oxide and/or butylene oxide units.

The hydrophobic end group portion (iii) of the associative monomer is a hydrocarbon moiety belonging to one of the following hydrocarbon classes: a $C_8$-$C_{30}$ linear alkyl, a $C_8$-$C_{30}$ branched alkyl, a $C_8$-$C_{30}$ carbocyclic alkyl, a $C_2$-$C_{30}$ alkyl-substituted phenyl, an araalkyl substituted phenyl, and aryl-substituted $C_2$-$C_{30}$ alkyl groups.

Non-limiting examples of suitable hydrophobic end group portions (iii) of the associative monomers are linear or branched alkyl groups having about 8 to about 30 carbon atoms, such as capryl ($C_8$), iso-octyl (branched $C_8$), decyl ($C_{10}$), lauryl ($C_{12}$), myristyl ($C_{14}$), cetyl ($C_{16}$), cetearyl ($C_{16}$-$C_{18}$), stearyl ($C_{18}$), isostearyl (branched $C_{18}$), arachidyl ($C_{20}$), behenyl ($C_{22}$), lignoceryl ($C_{24}$), cerotyl ($C_{26}$), montanyl ($C_{28}$), melissyl ($C_{30}$), and the like.

Examples of linear and branched alkyl groups having about 8 to about 30 carbon atoms that are derived from a natural source include, without being limited thereto, alkyl groups derived from hydrogenated peanut oil, soybean oil and canola oil (all predominately $C_{18}$), hydrogenated tallow oil ($C_{16}$-$C_{18}$), and the like; and hydrogenated $C_{10}$-$C_{30}$ terpenols, such as hydrogenated geraniol (branched $C_{10}$), hydrogenated farnesol (branched $C_{15}$), hydrogenated phytol (branched $C_{20}$), and the like.

Non-limiting examples of suitable $C_2$-$C_{30}$ alkyl-substituted phenyl groups include octylphenyl, nonylphenyl, decylphenyl, dodecylphenyl, hexadecylphenyl, octadecylphenyl, isooctylphenyl, sec-butylphenyl, and the like.

Exemplary aryl-substituted $C_2$-$C_{40}$ alkyl groups include, without limitation thereto, styryl (e.g., 2-phenylethyl), distyryl (e.g., 2,4-diphenylbutyl), tristyryl (e.g., 2,4,6-triphenylhexyl), 4-phenylbutyl, 2-methyl-2-phenylethyl, tristyrylphenolyl, and the like.

Suitable $C_5$-$C_{30}$ carbocyclic alkyl groups include, without being limited thereto, groups derived from sterols from animal sources, such as cholesterol, lanosterol, 7-dehydrocholesterol, and the like; from vegetable sources, such as phytosterol, stigmasterol, campesterol, and the like; and from yeast sources, such as ergosterol, mycosterol, and the like. Other carbocyclic alkyl hydrophobic end groups useful in the disclosed technology include, without being limited thereto, cyclooctyl, cyclododecyl, adamantyl, decahydronaphthyl, and groups derived from natural carbocyclic materials, such as pinene, hydrogenated retinol, camphor, isobornyl alcohol, and the like.

Useful associative monomers can be prepared by any method known in the art. See, for example, U.S. Pat. No. 4,421,902 to Chang et al.; U.S. Pat. No. 4,384,096 to Sonnabend; U.S. Pat. No. 4,514,552 to Shay et al.; U.S. Pat. No. 4,600,761 to Ruffner et al.; U.S. Pat. No. 4,616,074 to Ruffner; U.S. Pat. No. 5,294,692 to Barron et al.; U.S. Pat. No. 5,292,843 to Jenkins et al.; U.S. Pat. No. 5,770,760 to Robinson; and U.S. Pat. No. 5,412,142 to Wilkerson, III et al.; the pertinent disclosures of which are incorporated herein by reference.

In one aspect, exemplary associative monomers include those represented by formulas below:

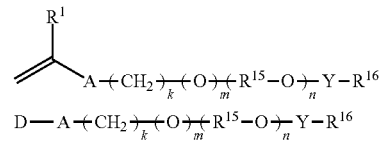

wherein $R^1$ is hydrogen or methyl; A is —$CH_2C(O)O$—, —$C(O)O$—, —$O$—, —$CH_2O$—, —$NHC(O)NH$—, —$C(O)NH$—, —Ar—$(CE_2)_z$-$NHC(O)O$—, —Ar—$(CE_2)_z$-$NHC(O)NH$—, or —$CH_2CH_2NHC(O)$—; Ar is a divalent arylene (e.g., phenylene); E is H or methyl; z is 0 or 1; k is an integer ranging from about 0 to about 30, and m is 0 or 1, with the proviso that when k is 0, m is 0, and when k is in the range of 1 to about 30, m is 1; D represents a vinyl or an allyl moiety; ($R^{15}$—$O$)$_n$ is a polyoxyalkylene moiety, which can be a homopolymer, a random copolymer, or a block copolymer of $C_2$-$C_4$ oxyalkylene units, $R^{15}$ is a divalent alkylene moiety selected from $C_2H_4$, $C_3H_6$, or $C_4H_8$, and combinations thereof; and n is an integer in the range of about 2 to about 150 in one aspect, from about 10 to about 120 in another aspect, and from about 15 to about 60 in a further aspect; Y is —$R^{15}O$—, —$R^{15}NH$—, —$C(O)$—, —$C(O)NH$—, —$R^{15}NHC(O)NH$—, or —$C(O)NHC(O)$—; $R^{16}$ is a substituted or unsubstituted alkyl selected from a $C_8$-$C_{30}$ linear alkyl, a $C_8$-$C_{30}$ branched alkyl, a $C_8$-$C_{30}$ carbocyclic alkyl, a $C_2$-$C_{30}$ alkyl-substituted phenyl, an araalkyl substituted phenyl, and an aryl-substituted $C_2$-$C_{30}$ alkyl; wherein the $R^{16}$ alkyl group, aryl group, phenyl group optionally comprises one or more substituents selected from the group consisting of a hydroxyl group, an alkoxyl group, benzyl group phenylethyl group, and a halogen group.

In one aspect, the hydrophobically modified associative monomer is an alkoxylated (meth)acrylate having a hydrophobic group containing 8 to 30 carbon atoms represented by the following formula:

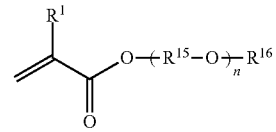

wherein $R^1$ is hydrogen or methyl; $R^{15}$ is a divalent alkylene moiety independently selected from $C_2H_4$, $C_3H_6$, and $C_4H_8$, and n represents an integer ranging from about 2 to about 150 in one aspect, from about 5 to about 120 in another aspect, and from about 10 to about 60 in a further aspect, ($R^{15}$—O) can be arranged in a random or a block configuration; $R^{16}$ is a substituted or unsubstituted alkyl selected from a $C_8$-$C_{30}$ linear alkyl, a $C_8$-$C_{30}$ branched alkyl, a $C_8$-$C_{30}$ carbocyclic alkyl, a $C_2$-$C_{30}$ alkyl-substituted phenyl, and an aryl-substituted $C_2$-$C_{30}$ alkyl.

Representative associative monomers under include lauryl polyethoxylated methacrylate (LEM), cetyl polyethoxylated methacrylate (CEM), cetearyl polyethoxylated methacrylate (CSEM), stearyl polyethoxylated (meth)acrylate, arachidyl polyethoxylated (meth)acrylate, behenyl polyethoxylated methacrylate (BEM), cerotyl polyethoxylated (meth)acrylate, montanyl polyethoxylated (meth)acrylate, melissyl polyethoxylated (meth)acrylate, phenyl polyethoxylated (meth)acrylate, nonylphenyl polyethoxylated (meth)acrylate, w-tristyrylphenyl polyoxyethylene methacrylate, where the polyethoxylated portion of the monomer contains about 2 to about 150 ethylene oxide units in one aspect, from about 5 to about 120 in another aspect, from about 10 to about 60 in still another aspect, from 10 to 40 in a further aspect, and from 15 to 30 in a still further aspect; octyloxy polyethyleneglycol (8) polypropyleneglycol (6) (meth)acrylate, phenoxy polyethylene glycol (6) polypropylene glycol (6) (meth)acrylate, and nonylphenoxy polyethylene glycol polypropylene glycol (meth)acrylate.

The semi-hydrophobic monomers of the disclosed technology are structurally similar to the associative monomer described above, but have a substantially non-hydrophobic end group portion. The semi-hydrophobic monomer has an ethylenically unsaturated end group portion (i) for addition polymerization with the other monomers of the disclosed technology; a polyoxyalkylene mid-section portion (ii) for imparting selective hydrophilic and/or hydrophobic properties to the product polymer and a semi-hydrophobic end group portion (iii). The unsaturated end group portion (i) supplying the vinyl or other ethylenically unsaturated end group for addition polymerization is preferably derived from an α,β-ethylenically unsaturated mono carboxylic acid. Alternatively, the end group portion (i) can be derived from an allyl ether residue, a vinyl ether residue or a residue of a nonionic urethane monomer.

The polyoxyalkylene mid-section (ii) specifically comprises a polyoxyalkylene segment, which is substantially similar to the polyoxyalkylene portion of the associative monomers described above. In one aspect, the polyoxyalkylene portions (ii) include polyoxyethylene, polyoxypropylene, and/or polyoxybutylene units comprising from about 2 to about 150 in one aspect, from about 5 to about 120 in another aspect, and from about 10 to about 60 in a further aspect of ethylene oxide, propylene oxide, and/or butylene oxide units, arranged in random or blocky sequences.

Optionally, at least one semi-hydrophobic monomer can be used in the preparation of the amphiphilic polymers of the disclosed technology. A semi-hydrophobic monomer is similar in structure to an associative monomer, but has a substantially non-hydrophobic end group selected from hydroxyl or a moiety containing 1 to 4 carbon atoms.

In one aspect, the semi-hydrophobic monomer can be represented by the following formulas:

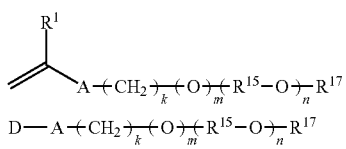

wherein $R^1$ is hydrogen or methyl; A is —CH$_2$C(O)O—, —C(O)O—, —O—, —CH$_2$O—, —NHC(O)NH—, —C(O)NH—, —Ar—(CE$_2$)$_z$-NHC(O)O—, —Ar—(CE$_2$)$_z$-NHC(O)NH—, or —CH$_2$CH$_2$NHC(O)—; Ar is a divalent arylene (e.g., phenylene); E is H or methyl; z is 0 or 1; k is an integer ranging from about 0 to about 30, and m is 0 or 1, with the proviso that when k is 0, m is 0, and when k is in the range of 1 to about 30, m is 1; (R$^{15}$—O)$_n$ is a polyoxyalkylene moiety, which can be a homopolymer, a random copolymer, or a block copolymer of C$_2$-C$_4$ oxyalkylene units, R$^{15}$ is a divalent alkylene moiety selected from C$_2$H$_4$, C$_3$H$_6$, or C$_4$H$_8$, and combinations thereof; and n is an integer in the range of about 2 to about 150 in one aspect, from about 5 to about 120 in another aspect, and from about 10 to about 60 in a further aspect; $R^{17}$ is selected from hydrogen and a linear or branched C$_1$-C$_4$ alkyl group (e.g., methyl, ethyl, propyl, iso-propyl, butyl, iso-butyl, and tert-butyl); and D represents a vinyl or an allyl moiety.

In one aspect, the semi-hydrophobic monomer can be represented by the following formulas:

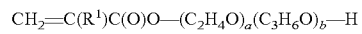

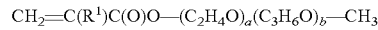

wherein $R^1$ is hydrogen or methyl, and "a" is an integer ranging from 0 or 2 to about 120 in one aspect, from about 5 to about 45 in another aspect, and from about 10 to about 25 in a further aspect, and "b" is an integer ranging from about 0 or 2 to about 120 in one aspect, from about 5 to about 45 in another aspect, and from about 10 to about 25 in a further aspect, subject to the proviso that "a" and "b" cannot be 0 at the same time.

Examples of semi-hydrophobic monomers include polyethyleneglycol methacrylate available under the product names Blemmer® PE-90 (R$^1$=methyl, a=2, b=0), PE-200 (R$^1$=methyl, a=4.5, b=0), and PE-350 (R$^1$=methyl a=8, b=0); polypropylene glycol methacrylate available under the product names Blemmer® PP-1000 (R$^1$=methyl, b=4-6, a=0), PP-500 (R$^1$=methyl, a=0, b=9), PP-800 (R$^1$=methyl, a=0, b=13); polyethyleneglycol polypropylene glycol methacrylate available under the product names Blemmer® 50PEP-300 (R$^1$=methyl, a=3.5, b=2.5), 70PEP-350B (R$^1$=methyl, a=5, b=2); polyethyleneglycol acrylate available under the product names Blemmer® AE-90 (R$^1$=hydrogen, a=2, b=0), AE-200 (R$^1$=hydrogen, a=2, b=4.5), AE-400 (R$^1$=hydrogen, a=10, b=0); polypropyleneglycol acrylate available under the product names Blemmer® AP-150 (R$^1$=hydrogen, a=0, b=3), AP-400 (R$^1$=hydrogen, a=0, b=6), AP-550 (R$^1$=hydrogen, a=0, b=9). Blemmer® is a trademark of NOF Corporation, Tokyo, Japan.

Additional examples of semi-hydrophobic monomers include methoxypolyethyleneglycol methacrylate available under the product names Visiomer® MPEG 750 MA W (R$^1$=methyl, a=17, b=0), MPEG 1005 MA W (R$^1$=methyl, a=22, b=0), MPEG 2005 MA W (R$^1$=methyl, a=45, b=0), and MPEG 5005 MA W (R$^1$=methyl, a=113, b=0) from Evonik Röhm GmbH, Darmstadt, Germany); Bisomer® MPEG 350 MA (R$^1$=methyl, a=8, b=0), and MPEG 550 MA (R$^1$=methyl, a=12, b=0) from GEO Specialty Chemicals, Ambler Pa.; Blemmer® PME-100 (R$^1$=methyl, a=2, b=0), PME-200 (R$^1$=methyl, a=4, b=0), PME400 (R$^1$=methyl, a=9, b=0), PME-1000 (R$^1$=methyl, a=23, b=0), PME-4000 (R$^1$=methyl, a=90, b=0).

In one aspect, the semi-hydrophobic monomer can be represented by the following formulas:

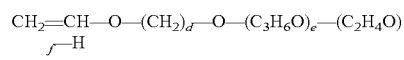

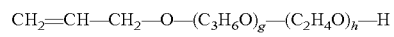

wherein d is an integer of 2, 3, or 4; e is an integer in the range of from about 1 to about 10 in one aspect, from about 2 to about 8 in another aspect, and from about 3 to about 7 in a further aspect; f is an integer in the range of from about 5 to about 50 in one aspect, from about 8 to about 40 in another aspect, and from about 10 to about 30 in a further aspect; g is an integer in the range of from 1 to about 10 in one aspect, from about 2 to about 8 in another aspect, and from about 3 to about 7 in a further aspect; and h is an integer in the range of from about 5 to about 50 in one aspect, and from about 8 to about 40 in another aspect; e, f, g, and h can be 0 subject to the proviso that e and f cannot be 0 at the same time, and g and h cannot be 0 at the same time.

Semi-hydrophobic monomers are commercially available under the trade names Emulsogen® R109, R208, R307, RAL109, RAL208, and RAL307 sold by Clariant Corporation; BX-AA-E5P5 sold by Bimax, Inc.; and combinations thereof. EMULSOGEN® R109 is a randomly ethoxylated/propoxylated 1,4-butanediol vinyl ether having the empirical formula $CH_2=CH-O(CH_2)_4O(C_3H_6O)_4(C_2H_4O)_{10}H$; Emulsogen® R208 is a randomly ethoxylated/propoxylated 1,4-butanediol vinyl ether having the empirical formula $CH_2=CH-O(CH_2)_4O(C_3H_6O)_4(C_2H_4O)_{20}H$; Emulsogen® R307 is a randomly ethoxylated/propoxylated 1,4-butanediol vinyl ether having the empirical formula $CH_2=CH-O(CH_2)_4O(C_3H_6O)_4(C_2H_4O)_{30}H$; Emulsogen® RAL109 is a randomly ethoxylated/propoxylated allyl ether having the empirical formula $CH_2=CHCH_2O(C_3H_6O)_4(C_2H_4O)_{10}H$; Emulsogen® RAL208 is a randomly ethoxylated/propoxylated allyl ether having the empirical formula $CH_2=CHCH_2O(C_3H_6O)_4(C_2H_4O)_{20}H$; Emulsogen® RAL307 is a randomly ethoxylated/propoxylated allyl ether having the empirical formula $CH_2=CHCH_2O(C_3H_6O)_4(C_2H_4O)_{30}H$; and BX-AA-E5P5 is a randomly ethoxylated/propoxylated allyl ether having the empirical formula $CH_2=CHCH_2O(C_3H_6O)_5(C_2H_4O)_5H$.

In the associative and semi-hydrophobic monomers of the disclosed technology, the polyoxyalkylene mid-section portion contained in these monomers can be utilized to tailor the hydrophilicity and/or hydrophobicity of the polymers in which they are included. For example, mid-section portions rich in ethylene oxide moieties are more hydrophilic while mid-section portions rich in propylene oxide moieties are more hydrophobic. By adjusting the relative amounts of ethylene oxide to propylene oxide moieties present in these monomers the hydrophilic and hydrophobic properties of the polymers in which these monomers are included can be tailored as desired.

The amount of associative and/or semi-hydrophobic monomer utilized in the preparation of the polymers of the disclosed technology can vary widely and depends, among other things, on the final rheological and aesthetic properties desired in the polymer. When utilized, the monomer reaction mixture contains one or more monomers selected from the associative and/or semi-hydrophobic monomers disclosed above in amounts ranging from about 0.01 to about 15 wt. % in one aspect, from about 0.1 wt. % to about 10 wt. % in another aspect, from about 0.5 to about 8 wt. % in still another aspect and from about 1, 2 or 3 to about 5 wt. % in a further aspect, based on the weight of the total monomers.

Ionizable Monomer

In one aspect of the disclosed technology, the crosslinked, nonionic, amphiphilic polymer compositions of the disclosed technology can be polymerized from a monomer composition including from about 0 to about 15.0 wt. % in one aspect, from about 0.1 to about 15 wt. % in another aspect, from about 0.5 to about 10 wt. % in still another aspect, from about 1 to about 8 wt. % in a further aspect, and from about 2 or 3 to about 5 wt. % in a still further aspect of an ionizable and/or ionized monomer, based on the weight of the total monomers, so long as the yield stress value or clarity of the yield stress fluids in which the polymers of the disclosed technology are included are not deleteriously affected (i.e., the yield stress value of the fluid does not fall below 1 mPa, or 0.1 Pa).

In another aspect, the amphiphilic polymer compositions of the disclosed technology can be polymerized from a monomer composition comprising less than 3 wt. % in one aspect, less than 1 wt. % in a further aspect, less than 0.5 wt. % in a still further aspect, less than 0.1 wt. % in an additional aspect, and less than 0.05 wt. % in a further aspect, of an ionizable and/or an ionized moiety, based on the weight of the total monomers.

Ionizable monomers include monomers having a base neutralizable moiety and monomers having an acid neutralizable moiety. Base neutralizable monomers include olefinically unsaturated monocarboxylic and dicarboxylic acids and their salts containing 3 to 5 carbon atoms and anhydrides thereof. Examples include (meth)acrylic acid, itaconic acid, maleic acid, maleic anhydride, and combinations thereof. Other acidic monomers include styrenesulfonic acid, 2-acrylamido-2-methylpropane sulfonic acid (AMPS® monomer), vinylsulfonic acid, vinylphosphonic acid, allylsulfonic acid, methallylsulfonic acid; and salts thereof.

Acid neutralizable monomers include olefinically unsaturated monomers which contain a basic nitrogen atom capable of forming a salt or a quaternized moiety upon the addition of an acid. For example, these monomers include vinylpyridine, vinylpiperidine, vinylimidazole, vinylmethylimidazole, dimethylaminomethyl (meth)acrylate, dimethylaminoethyl (meth)acrylate, diethylaminomethyl (meth)acrylate and methacrylate, dimethylaminoneopentyl (meth)acrylate, dimethylaminopropyl (meth)acrylate, and diethylaminoethyl (meth)acrylate.

Crosslinking Monomer

The crosslinking monomer is an amphiphilic crosslinking agent. The amphiphilic crosslinking agent is utilized to polymerize covalent crosslinks into the amphiphilic polymer backbone. In some instances, conventional crosslinking agents can affect the volume expansion or swelling of micro-gel particles in fluids containing surfactants. For example, a high level of conventional crosslinking agent could provide a high yield stress but the limited expansion of the micro-gels would result in undesirably high polymer use levels and low optical clarity. On the other hand, a low level of conventional crosslinking agents could give high optical clarity but low yield stress. It is desirable that polymeric micro-gels allow maximum swelling while maintaining a desirable yield stress, and it has been found that the use of amphiphilic crosslinking agents in place of, or in conjunction with conventional crosslinking agents can provide just these benefits. In addition, it has been found that the amphiphilic crosslinking agent can be easily reacted into the amphiphilic polymer. Often, certain processing techniques, such as staging, can be required with conventional crosslinking agents to achieve the proper balance of optical clarity and yield stress. In contrast, it has been found that amphiphilic crosslinking agents can simply be added in a single stage with the monomer mixture.

Amphiphilic crosslinking agents are a subset of compounds known in the art as reactive surfactants. Reactive surfactants are surface acting agents containing at least one reactive moiety so that they can covalently link to the surface of polymeric particles. By linking to particles, the reactive surfactants can improve the colloidal stability of latex particles due to the surfactant's resistance to desorbing from the particle surface. Reactive surfactants in the art commonly only have, or only need, one reactive moiety to prevent such desorption.

In one aspect, exemplary amphiphilic crosslinking agents suitable for use with the present technology can include, but not be limited to, compounds such as those disclosed in US 2013/0047892 (published Feb. 28, 2013 to Palmer, Jr. et al.), represented by the following formulas:

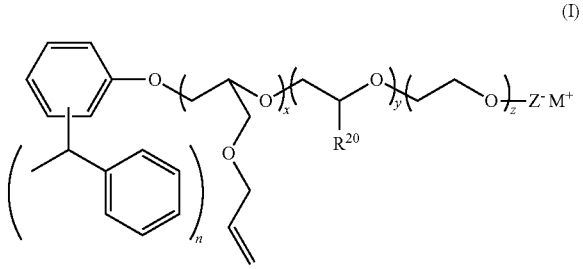

where $R^{20}=CH_3$, $CH_2CH_3$, $C_6H_5$, or $C_{14}H_{29}$, n=1, 2, or 3; x is 2-10, y is 0-200, z is 4-200, more preferably from about 5 to 60, and most preferably from about 5 to 40; Z can be either $SO_3^-$ or $PO_3^{2-}$, and $M^+$ is $Na^+$, $K^+$, $NH_4^+$, or an alkanolamine such as, for example, monoethanolamine, diethanolamine, and triethanolamine;

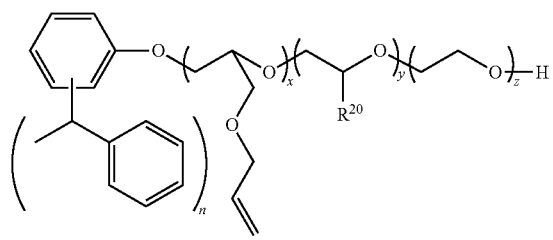

where $R^{20}=CH_3$, $CH_2CH_3$, $C_6H_5$, or $C_{14}H_{29}$; n=1, 2, 3; x is 2-10, y is 0-200, z is 4-200, more preferably from about 5 to 60, and most preferably from about 5 to 40;

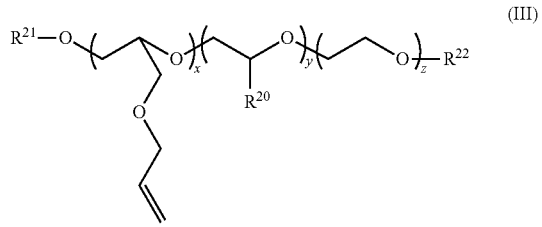

where $R^{21}$ is a $C_{10-24}$ alkyl, alkaryl, alkenyl, or cycloalkyl, $R^{20}=CH_3$, $CH_2CH_3$, $C_6H_5$, or $C_{14}H_{29}$; x is 2-10, y is 0-200, z is 4-200, more preferably from about 5 to 60, and most preferably from about 5 to 40; and $R^{22}$ is H or $Z^- M^+$ Z can be either $SO_3^-$ or $PO_3^{2-}$, and $M^+$ is $Na^+$, $K^+$, $NH_4^+$, or an alkanolamine such as, for example, monoethanolamine, diethanolamine, and triethanolamine.

In one embodiment, the amphiphilic crosslinking agent can be used in an amount ranging from about 0.01 to about 3 wt. % in one aspect, from about 0.05 to about 0.1 wt. % in another aspect, and from about 0.1 to about 0.9 wt. % in a further aspect, based on the total weight of the monounsaturated monomers utilized to prepare the nonionic, amphiphilic polymers of the disclosed technology. Stated another way, the amount of amphiphilic crosslinking agent and/or conventional crosslinking monomer discussed below can be calculated on the basis of parts by wt. (100% active material) per 100 parts by wt. (100% active material) of total monounsaturated monomers utilized to prepare the polymer of the disclosed technology.

In another embodiment, the amphiphilic crosslinking agent can contain an average of about 1.5 or 2 unsaturated moieties and can be used in an amount ranging from about 0.01 to about 3 parts by wt. % in one aspect, from about 0.02 to about 1 parts by wt. % in another aspect, from about 0.05 to about 0.9 parts by wt. % in a further aspect, and from about 0.075 to about 0.5 wt. % parts by wt. in a still further aspect, and from about 0.1 to about 0.15 parts by wt. % in another aspect, based upon 100 parts by wt. of monounsaturated monomers utilized to prepare the nonionic, amphiphilic polymers of the disclosed technology.

In one aspect, the amphiphilic crosslinking agent is selected from compounds of formulas (III), (IV) or (V).

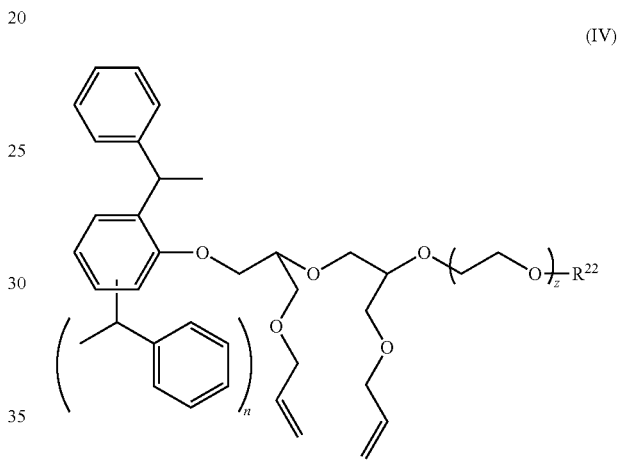

where n is 1 or 2; z is 4 to 40 in one aspect, 5 to 38 in another aspect, and 10 to 20 in a further aspect; and R4 is H, $SO_3^-M^+$ or $PO_3^{-2} M^+$, and M is selected from Na, K, and $NH_4$.

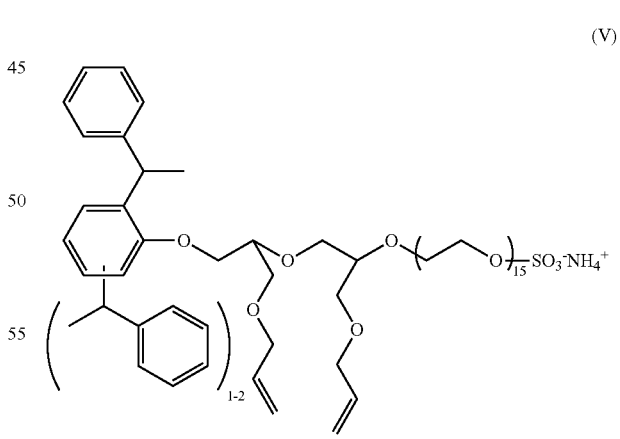

The foregoing amphiphilic crosslinking agents conforming to formulas (I), (II), (III), (IV) and (V) are disclosed in U.S. Patent Application Publication No. US 2014/0114006, the disclosure of which is herein incorporated by reference, and are commercially available under the E-Sperse™ RS Series trade name (e.g., product designations RS-1617, RS-1618, RS-1684) from Ethox Chemicals, LLC.

In one embodiment, the crosslinking monomer can include a combination of an amphiphilic crosslinking agent and a conventional crosslinking agent. These are relatively low molecular weight polyunsaturated compounds (less than 300 Daltons). In one aspect, the conventional crosslinking agent is a polyunsaturated compound containing at least 2 unsaturated moieties. In another aspect, the conventional crosslinking agent contains at least 3 unsaturated moieties. Exemplary polyunsaturated compounds include di(meth)acrylate compounds such as ethylene glycol di(meth)acrylate, polyethylene glycol di(meth)acrylate, triethylene glycol di(meth)acrylate, 1,3-butylene glycol di(meth)acrylate, 1,6-butylene glycol di(meth)acrylate, 1,6-hexanediol di(meth)acrylate, neopentyl glycol di(meth)acrylate, 1,9-nonanediol di(meth)acrylate, 2,2'-bis(4-(acryloxy-propyloxyphenyl) propane, and 2,2'-bis(4-(acryloxydiethoxy-phenyl)propane; tri(meth)acrylate compounds such as, trimethylolpropane tri(meth)acrylate, trimethylolethane tri(meth)acrylate, and tetramethylolmethane tri(meth)acrylate; tetra(meth)acrylate compounds such as ditrimethylolpropane tetra(meth)acrylate, tetramethylolmethane tetra(meth)acrylate, and pentaerythritol tetra(meth)acrylate; hexa(meth)acrylate compounds such as dipentaerythritol hexa(meth)acrylate; allyl compounds such as allyl (meth)acrylate, diallylphthalate, diallyl itaconate, diallyl fumarate, and diallyl maleate; polyallyl ethers of sucrose having from 2 to 8 allyl groups per molecule, polyallyl ethers of pentaerythritol such as pentaerythritol diallyl ether, pentaerythritol triallyl ether, and pentaerythritol tetraallyl ether, and combinations thereof; polyallyl ethers of trimethylolpropane such as trimethylolpropane diallyl ether, trimethylolpropane triallyl ether, and combinations thereof. Other suitable polyunsaturated compounds include divinyl glycol, divinyl benzene, and methylenebisacrylamide.

In another aspect, suitable polyunsaturated monomers can be synthesized via an esterification reaction of a polyol made from ethylene oxide or propylene oxide or combinations thereof with unsaturated anhydride such as maleic anhydride, citraconic anhydride, itaconic anhydride, or an addition reaction with unsaturated isocyanate such as 3-isopropenyl-α-α-dimethylbenzene isocyanate.

Mixtures of two or more of the foregoing polyunsaturated compounds can also be utilized to crosslink the nonionic, amphiphilic polymers. In one aspect, the mixture of conventional unsaturated crosslinking monomer contains an average of 2 unsaturated moieties. In another aspect, the mixture of conventional crosslinking agents contains an average of 2.5 unsaturated moieties. In still another aspect, the mixture of conventional crosslinking agents contains an average of about 3 unsaturated moieties. In a further aspect, the mixture of conventional crosslinking agents contains an average of about 3.5 unsaturated moieties.

In one embodiment, the conventional crosslinking agent component can be used in an amount ranging from about 0.01 to about 1 parts by wt. in one aspect, from about 0.05 to about 0.75 parts by wt. in another aspect, and from about 0.1 to about 0.5 parts by wt. in a further aspect, based on 100 parts by wt. of the monounsaturated monomers utilized to prepare the nonionic, amphiphilic polymers of the disclosed technology.

In another embodiment of the disclosed technology, the conventional crosslinking agent component contains an average of about 3 unsaturated moieties and can be used in an amount ranging from about 0.01 to about 0.3 parts by wt. in one aspect, from about 0.02 to about 0.25 parts by wt. in another aspect, from about 0.05 to about 0.2 parts by wt. in a further aspect, and from about 0.075 to about 0.175 parts by wt. in a still further aspect, and from about 0.1 to about 0.15 parts by wt. in another aspect, based on 100 parts by wt. of the monounsaturated monomers utilized to prepare the nonionic, amphiphilic polymers of the disclosed technology.

In one aspect, the conventional crosslinking agent is selected from trimethylolpropane tri(meth)acrylate, trimethylolethane tri(meth)acrylate, tetramethylolmethane tri(meth)acrylate, pentaerythritol triallylether and polyallyl ethers of sucrose having 3 allyl groups per molecule.

In another aspect, the nonionic amphiphilic polymer can be crosslinked with a combination of a conventional crosslinking agent and an amphiphilic crosslinking agent. The conventional crosslinking agent and amphiphilic crosslinking agent can be used in a total amount ranging from about 0.01 to about 1 parts by wt. in one aspect, from about 0.05 to about 0.75 parts by wt. in another aspect, and from about 0.1 to about 0.5 parts by wt. in a further aspect, based on 100 parts by wt. of the monounsaturated monomers utilized to prepare the nonionic, amphiphilic polymers of the disclosed technology.

In another embodiment, the combination of the conventional crosslinking agent and amphiphilic crosslinking agent can contain an average of about 2 or 3 unsaturated moieties and can be used in an amount ranging from about 0.01 to about 2 parts by wt. in one aspect, from about 0.02 to about 0.3 parts by wt. in another aspect, from about 0.05 to about 0.2 parts by wt. in a further aspect, and from about 0.075 to about 0.175 parts by wt. in a still further aspect, and from about 0.1 to about 0.15 parts by wt. in another aspect, based 100 parts by wt. of the of the monounsaturated monomers utilized to prepare the nonionic, amphiphilic polymer of the disclosed technology.

In one aspect, the combination of the conventional crosslinking agent and amphiphilic crosslinking agent can include conventional crosslinking agents selected from selected from trimethylolpropane tri(meth)acrylate, trimethylolethane tri(meth)acrylate, tetramethylolmethane tri(meth)acrylate, pentaerythritol triallylether and polyallyl ethers of sucrose having 3 allyl groups per molecule, and combinations thereof, and amphiphilic crosslinking agents selected from compounds of formula (III), (V), and combinations thereof.

Amphiphilic Additive

In accordance with one aspect of the present technology the amphiphilic additive is mixed into the polymerizable monomer mixture containing the amphiphilic crosslinking agent before introducing the monomer mixture into the polymerization medium. The monomer mixture (disperse phase) as well as the polymerization medium (continuous phase) is devoid of a protective colloid such as, for example, poly(vinyl alcohol) and poly(vinyl acetate) as exemplified in WO 2015/095286 and WO 2016/100183 and/or a polymeric steric stabilizer. Surprisingly, it has been found that by mixing an amphiphilic additive with the polymerizable monomer mixture and removing the protective colloid from the emulsion polymerization medium the clarity and turbidity properties of surfactant compositions containing the resultant polymer product is improved.

The amphiphilic additives of the present technology are nonionic and contain at least one hydrophilic segment and at least two hydrophobic segments.

In one embodiment the amphiphilic additive of the present technology is represented by the formula:

(X)

wherein Q represents a polyol residue; A represents a poly(ethylene glycol) residue; R is selected from a saturated and unsaturated $C_{10}$ to $C_{22}$ acyl group and a poly(propylene glycol) residue; $R^{23}$ is independently selected from H, a saturated and unsaturated $C_{10}$ to $C_{22}$ acyl radical and a poly(propylene glycol) residue; a is 0 or 1; b is 0 or 1; and c is a number from 1 to 4; subject to the proviso that when b is 0, a and c are 1, and when b is 1, a is 0 and $R^{23}$ is not a poly(propylene glycol) residue.

In one aspect of the disclosed technology, the amphiphilic additive is a polyethoxylated alkyl glucoside ester represented by the formula:

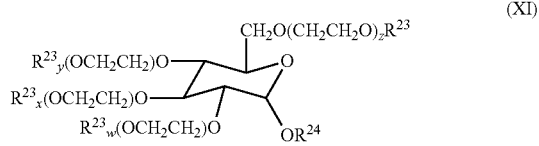

(XI)

wherein $R^{23}$ is independently selected from H and a saturated and unsaturated $C_{10}$-$C_{22}$ acyl group; $R^{24}$ is selected from a $C_1$-$C_{10}$ alkyl group; and the sum of w+x+y+z ranges from about 60 to about 150 in one aspect, from about 80 to about 135 in another aspect, and from about 90 to about 125 in a further aspect, and from about 100 to about 120 in a still further aspect; subject to the proviso that at no more than two of $R^{23}$ can be H at the same time.

In one aspect $R^{23}$ is an acyl residue of lauric acid, myristic acid, palmitic acid, palmitoleic acid, steric acid, isostearic acid, oleic acid, ricinoleic acid vaccenic acid, linoleic acid (alpha and gamma), arachidic acid, behenic acid, and mixtures thereof and $R^{25}$ is methyl.

Suitable polyethoxylated alkyl glucoside esters are commercially available under the trade names Glucamate™ LT (INCI Name: PEG-120 Methyl Glucose Trioleate (and) Propylene Glycol (and) Water), Glucamate™ VLT (INCI Name: PEG-120 Methyl Glucose Trioleate (and) Propanediol), and Glucamate™ DOE-120 (INCI Name: PEG-120 Methyl Glucose Dioleate).

In one aspect of the disclosed technology, the amphiphilic additive is selected from a poly(ethylene glycol) diester where poly(ethylene glycol) (PEG) is esterified with a saturated and unsaturated $C_{10}$ to $C_{22}$ fatty acid is represented by the formula:

(XII)

wherein B is independently selected from a saturated and unsaturated $C_{10}$ to $C_{22}$ acyl radical; and n ranges from about 10 to about 120 in one aspect, from about 12 to about 110 in another aspect, and from about 15 to about 100 in a further aspect.

In one aspect B is an acyl residue of lauric acid, myristic acid, palmitic acid, palmitoleic acid, steric acid, isostearic acid, oleic acid, ricinoleic acid vaccenic acid, linoleic acid (alpha and gamma), arachidic acid, behenic acid, and mixtures thereof.

Exemplary PEG diesters include but are not limited to the laurate, palmitate, palmitoleate, stearate, isostearate, and oleate diesters of PEG-400, PEG-600, PEG-1000, PEG-2000, and PEG-4000.

In one aspect of the disclosed technology, the amphiphilic additive is a poly(propylene glycol)-block-poly(ethylene glycol)-block-poly(propylene glycol)-block copolymer represented by the formula:

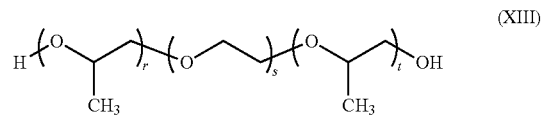

(XIII)

wherein r=t and range from about 5 to about 20 in one aspect, from about 6 to about 15 in another aspect, and from about 8 to about 14 in a further aspect; and s ranges from about 20 to about 30 in one aspect from about 21 to about 27 in another aspect and from about 23 to about 25 in a further aspect.

In one aspect, the poly(propylene glycol)-block-poly(ethylene glycol)-block-poly(propylene glycol)-block copolymer has a number average molecular weight ranging from about 1500 to about 3500 Da.

The poly(propylene glycol)-block-poly(ethylene glycol)-block-poly(propylene glycol)-block copolymer contains from about 35 to about 60 in one aspect, from about 40 to about 55 wt. % in another aspect, and from about 45 to about 50 wt. % in still another aspect of poly(ethylene glycol). Suitable poly(propylene glycol)-block-poly(ethylene glycol)-block-poly(propylene glycol)-block copolymers are marketed under the Pluronic™ 10R5 and Pluronic™ 17R4 trade names by BASF Corporation, Florham Park, N.J.

The amount of amphiphilic additive that is mixed with the polymerizable monomer mixture ranges from about 1 to about 15 parts by wt. in one aspect, from about 2 to about 10 parts by wt. in another aspect, and from about 3 to about 6 parts by wt. in still another aspect, based upon 100 parts by wt. of the monounsaturated monomers utilized to prepare the nonionic, amphiphilic polymers of the disclosed technology.

Amphiphilic Polymer Synthesis

The crosslinked, nonionic, amphiphilic polymer of the disclosed technology can be made using conventional free-radical emulsion polymerization techniques. The polymerization processes are carried out in the absence of oxygen under an inert atmosphere such as nitrogen. The polymerization can be carried out in a suitable solvent system such as water. Minor amounts of a hydrocarbon solvent, organic solvent, as well as mixtures thereof can be employed. The polymerization reactions are initiated by any means which results in the generation of a suitable free-radical. Thermally derived radicals, in which the radical species is generated from thermal, homolytic dissociation of peroxides, hydroperoxides, persulfates, percarbonates, peroxyesters, hydrogen peroxide and azo compounds can be utilized. The initiators can be water soluble or water insoluble depending on the solvent system employed for the polymerization reaction.

The initiator compounds can be utilized in an amount of up to 30 wt. % in one aspect, 0.01 to 10 wt. % in another aspect, and 0.2 to 3 wt. % in a further aspect, based on the total weight of the dry polymer.

Exemplary free radical water soluble initiators include, but are not limited to, inorganic persulfate compounds, such as ammonium persulfate, potassium persulfate, and sodium persulfate; peroxides such as hydrogen peroxide, benzoyl peroxide, acetyl peroxide, and lauryl peroxide; organic hydroperoxides, such as cumene hydroperoxide and t-butyl hydroperoxide; organic peracids, such as peracetic acid, and water soluble azo compounds, such as 2,2'-azobis(tert-alkyl) compounds having a water solubilizing substituent on the alkyl group. Exemplary free radical oil soluble compounds include, but are not limited to 2,2'-azobisisobutyronitrile, and the like. The peroxides and peracids can optionally be activated with reducing agents, such as sodium bisulfite, sodium formaldehyde, or ascorbic acid, transition metals, hydrazine, and the like. In one aspect, azo polymerization catalysts include the Vazo® free-radical polymerization initiators, available from DuPont, such as Vazo® 44 (2,2'-azobis(2-(4,5-dihydroimidazolyl)propane), Vazo® 56 (2,2'-azobis(2-methylpropionamidine) dihydrochloride), Vazo® 67 (2,2'-azobis(2-methylbutyronitrile)), and Vazo® 68 (4,4'-azobis(4-cyanovaleric acid)).

Optionally, the use of known redox initiator systems as polymerization initiators can be employed. Such redox initiator systems include an oxidant (initiator) and a reductant. Suitable oxidants include, for example, hydrogen peroxide, sodium peroxide, potassium peroxide, t-butyl hydroperoxide, t-amyl hydroperoxide, cumene hydroperoxide, sodium perborate, perphosphoric acid and salts thereof, potassium permanganate, and ammonium or alkali metal salts of peroxydisulfuric acid, typically at a level of 0.01% to 3.0% by weight, based on dry polymer weight, are used. Suitable reductants include, for example, alkali metal and ammonium salts of sulfur-containing acids, such as sodium sulfite, bisulfite, thiosulfate, hydrosulfite, sulfide, hydrosulfide or dithionite, formadinesulfinic acid, hydroxymethanesulfonic acid, acetone bisulfite, amines such as ethanolamine, glycolic acid, glyoxylic acid hydrate, ascorbic acid, isoascorbic acid, lactic acid, glyceric acid, malic acid, 2-hydroxy-2-sulfinatoacetic acid, tartaric acid and salts of the preceding acids typically at a level of 0.01% to 3.0% by weight, based on dry polymer weight, is used. In one aspect, combinations of peroxodisulfates with alkali metal or ammonium bisulfites can be used, for example, ammonium peroxodisulfate and ammonium bisulfite. In another aspect, combinations of hydrogen peroxide containing compounds (t-butyl hydroperoxide) as the oxidant with ascorbic or erythorbic acid as the reductant can be utilized. The ratio of peroxide-containing compound to reductant is within the range from 30:1 to 0.05:1.

The polymerization reaction can be carried out at temperatures ranging from 20 to 200° C. in one aspect, from 50 to 150° C. in another aspect, and from 60 to 100° C. in a further aspect.

In one aspect, the polymerization can be carried out the presence of a chain transfer agent. Suitable chain transfer agents include, but are not limited to, thio- and disulfide containing compounds, such as $C_1$-$C_{18}$ alkyl mercaptans, such as tert-butyl mercaptan, n-octyl mercaptan, n-dodecyl mercaptan, tert-dodecyl mercaptan hexadecyl mercaptan, dodecyl mercaptan, octadecyl mercaptan; mercaptoalcohols, such as 2-mercaptoethanol, 2-mercaptopropanol; mercaptocarboxylic acids, such as mercaptoacetic acid and 3-mercaptopropionic acid; mercaptocarboxylic acid esters, such as butyl thioglycolate, isooctyl thioglycolate, dodecyl thioglycolate, isooctyl 3-mercaptopropionate, and butyl 3-mercaptopropionate; thioesters; $C_1$-$C_{18}$ alkyl disulfides; aryldisulfides; polyfunctional thiols such as trimethylolpropane-tris-(3-mercaptopropionate), pentaerythritol-tetra-(3-mercaptopropionate), pentaerythritol-tetra-(thioglycolate), pentaerythritol-tetra-(thiolactate), dipentaerythritol-hexa-(thioglycolate), and the like; phosphites and hypophosphites; $C_1$-$C_4$ aldehydes, such as formaldehyde, acetaldehyde, propionaldehyde; haloalkyl compounds, such as carbon tetrachloride, bromotrichloromethane, and the like; hydroxy-lammonium salts such as hydroxylammonium sulfate; formic acid; sodium bisulfite; isopropanol; and catalytic chain transfer agents such as, for example, cobalt complexes (e.g., cobalt (II) chelates).

The chain transfer agents are generally used in amounts ranging from 0.1 to 10 wt. %, based on the total weight of the monomers present in the polymerization medium.

Emulsion Process

In one exemplary aspect of the disclosed technology, the crosslinked, nonionic, amphiphilic polymer is polymerized via an emulsion process. The emulsion process can be conducted in a single reactor or in multiple reactors as is well-known in the art. The monomers can be added as a batch mixture or each monomer can be metered into the reactor in a staged process. A typical mixture in emulsion polymerization comprises water, monomer(s), an initiator (usually water-soluble) and an emulsifier. The monomers may be emulsion polymerized in a single-stage, two-stage or multi-stage polymerization process according to well-known methods in the emulsion polymerization art. In a two-stage polymerization process, the first stage monomers are added and polymerized first in the aqueous medium, followed by addition and polymerization of the second stage monomers. The aqueous medium optionally can contain an organic solvent. If utilized, the organic solvent is less than about 5 wt. % of the aqueous medium. Suitable examples of water-miscible organic solvents include, without limitation, esters, alkylene glycol ethers, alkylene glycol ether esters, lower molecular weight aliphatic alcohols, and the like.

To facilitate emulsification of the monomer mixture, the emulsion polymerization is carried out in the presence of at least one stabilizing surfactant. The term "stabilizing surfactant" is used in the context of surfactants employed to facilitate emulsification. In one embodiment, the emulsion polymerization is carried out in the presence of stabilizing surfactant (active weight basis) ranging in the amount of about 0.2% to about 5% by weight in one aspect, from about 0.5% to about 3% in another aspect, and from about 1% to about 2% by weight in a further aspect, based on a total monomer weight basis. The emulsion polymerization reaction mixture also includes one or more free radical initiators which are present in an amount ranging from about 0.01% to about 3% by weight based on total monomer weight. The polymerization can be performed in an aqueous or aqueous alcohol medium. Stabilizing surfactants for facilitating the emulsion polymerization include anionic, nonionic, amphoteric, and cationic surfactants, as well as reactive derivatives thereof, and mixtures thereof. By "reactive derivatives thereof" it is meant surfactants, or mixtures of surfactants, having on average less than one reactive moiety. Most commonly, anionic and nonionic surfactants can be utilized as stabilizing surfactants as well as mixtures thereof.

Suitable anionic surfactants for facilitating emulsion polymerization are well known in the art and include, but are not limited to ($C_6$-$C_{18}$) alkyl sulfates, ($C_6$-$C_{18}$) alkyl ether sulfates (e.g., sodium lauryl sulfate and sodium laureth sulfate), amino and alkali metal salts of dodecylbenzenesulfonic acid, such as sodium dodecyl benzene sulfonate and dimethylethanolamine dodecylbenzenesulfonate, sodium ($C_6$-$C_{16}$) alkyl phenoxy benzene sulfonate, disodium ($C_6$-$C_{16}$) alkyl phenoxy benzene sulfonate, disodium ($C_6$-$C_{16}$) di-alkyl phenoxy benzene sulfonate, disodium laureth-3 sulfosuccinate, sodium dioctyl sulfosuccinate, sodium di-sec-butyl naphthalene sulfonate, disodium dodecyl diphenyl ether sulfonate, disodium n-octadecyl sulfosuccinate, phosphate esters of branched alcohol ethoxylates, and the like, as well as reactive derivatives thereof.

Nonionic surfactants suitable for facilitating emulsion polymerizations are well known in the polymer art, and include, without limitation, linear or branched $C_8$-$C_{30}$ fatty alcohol ethoxylates, such as capryl alcohol ethoxylate, lauryl alcohol ethoxylate, myristyl alcohol ethoxylate, cetyl alcohol ethoxylate, stearyl alcohol ethoxylate, cetearyl alcohol ethoxylate, sterol ethoxylate, oleyl alcohol ethoxylate, and, behenyl alcohol ethoxylate; alkylphenol alkoxylates, such as octylphenol ethoxylates; and polyoxyethylene polyoxypropylene block copolymers, and the like, as well as reactive derivatives thereof. Additional fatty alcohol ethoxylates suitable as non-ionic surfactants are described below. Other useful nonionic surfactants include $C_8$-$C_{22}$ fatty acid esters of polyoxyethylene glycol, ethoxylated mono- and diglycerides, sorbitan esters and ethoxylated sorbitan esters, $C_8$-$C_{22}$ fatty acid glycol esters, block copolymers of ethylene oxide and propylene oxide, and combinations thereof, as well as reactive derivatives thereof. The number of ethylene oxide units in each of the foregoing ethoxylates can range from 2 and above in one aspect, and from 2 to about 150 in another aspect.

Optionally, other emulsion polymerization additives and processing aids which are well known in the emulsion polymerization art, such as solvents, buffering agents, chelating agents, inorganic electrolytes, biocides, and pH adjusting agents can be included in the polymerization system.

In one aspect a two stage emulsion polymerization reaction is utilized to prepare the polymers of the present technology. A mixture of the monounsaturated monomers, the amphiphiphilic crosslinking agent and the amphiphilic additive is added to a first reactor under inert atmosphere to a solution of emulsifying surfactant (e.g., anionic surfactant) in water. The monomer mixture is devoid of a protective colloid and/or a polymeric steric stabilizer such as poly (vinyl alcohol or poly(vinyl acetate). The contents of the first reactor are agitated to prepare a monomer emulsion (disperse phase). To a second reactor equipped with an agitator, an inert gas inlet, and feed pumps are added under inert atmosphere a desired amount of water and additional anionic surfactant (dispersing medium or continuous phase). In one aspect, no protective colloids and/or steric stabilizers are utilized in the dispersing medium). The contents of the second reactor are heated with mixing agitation. After the contents of the second reactor reaches a temperature in the range of about 55 to 98° C., a free radical initiator is injected into the aqueous surfactant solution, and the monomer emulsion from the first reactor is gradually metered into the second reactor over a period typically ranging from about one half to about four hours. The reaction temperature is controlled in the range of about 45 to about 95° C. After completion of the monomer addition, an additional quantity of free radical initiator can optionally be added to the second reactor, and the resulting reaction mixture is typically held at a temperature of about 45 to 95° C. for a time period sufficient to complete the polymerization reaction to obtain the polymer emulsion.

In one aspect, the crosslinked, nonionic, amphiphilic polymers of the disclosed technology are selected from an emulsion polymer polymerized from a monomer mixture comprising from about 20 to about 60 wt. % of at least one $C_1$-$C_5$ hydroxyalkyl (meth)acrylate; from about 10 to about 50 wt. % of at least one $C_1$-$C_5$ alkyl (meth)acrylate; from about 0, 0.1, 1, 5, or 7 to about 15 wt. % of at least one associative and/or a semi-hydrophobic monomer (wherein all monomer weight percentages are based on the total weight of the monounsaturated monomers); and from about 0.01 to about 5 parts by wt. in one aspect, from about 0.1 to about 3 parts by wt. in another aspect, and from about 0.5 to about 1 parts by wt. in a further aspect of at least one amphiphilic crosslinker (based upon 100 parts by wt. of the monounsaturated monomers utilized to prepare the polymer), and from about 1 to about 15 parts by wt. in one aspect, from about 2 to 10 parts by wt. in another aspect, and from about 3 to 6 parts by wt. in a further aspect of at least one amphiphilic additive (based upon 100 parts by wt. of the monounsaturated monomers utilized to prepare the polymer).

In one aspect, the crosslinked, nonionic, amphiphilic polymers of the disclosed technology are selected from an emulsion polymer polymerized from a monomer mixture comprising from about 20 to 50 wt. % of hydroxyethyl methacrylate; from about 10 to about 30 wt. % ethyl acrylate; from about 10 to about 35 wt. % butyl acrylate; from about 1 to about 10 or 15 wt. % of at least one associative and/or semi-hydrophobic monomer (wherein all monomer weight percentages are based on the weight of the total monomers); and from about 0.01 to about 5 parts by wt. in one aspect, from about 0.1 to about 3 parts by wt. in another aspect, and from about 0.5 to about 1 parts by wt. in a further aspect of at least one amphiphilic crosslinker (based on 100 parts by wt. of the monounsaturated monomers utilized to prepare the polymer), and from about 1 to about 15 parts by wt. in one aspect, from about 2 to 10 parts by wt. in another aspect, and from about 3 to 6 parts by wt. in a further aspect of at least one amphiphilic additive (based upon 100 parts by wt. of the monounsaturated monomers utilized to prepare the polymer).

In one aspect, the crosslinked, nonionic, amphiphilic polymers of the disclosed technology are selected from an emulsion polymer polymerized from a monomer mixture comprising from about 40 to 50 wt. % of hydroxyethyl methacrylate; from about 10 to about 20 wt. % ethyl acrylate; from about 20 to about 30 wt. % butyl acrylate; from about 5 or 6 to about 15 wt. % of at least one associative monomer selected from lauryl polyethoxylated (meth)acrylate, cetyl polyethoxylated (meth)acrylate, cetearyl polyethoxylated (meth)acrylate, stearyl polyethoxylated (meth)acrylate, arachidyl polyethoxylated (meth)acrylate, behenyl polyethoxylated (meth)acrylate, cerotyl polyethoxylated (meth)acrylate, montanyl polyethoxylated (meth)acrylate, melissyl polyethoxylated (meth)acrylate, where the polyethoxylated portion of the monomer contains about 2 to about 50 ethylene oxide units (wherein all monomer weight percentages are based on the weight of the total monomers); and from about 0.01 to about 5 parts by wt. in one aspect, from about 0.1 to about 3 parts by wt. in another aspect, and from about 0.5 to about 1 parts by wt. in a further aspect of at least one crosslinker (based on 100 parts by wt. of the monounsaturated monomers utilized to prepare the polymer), and from about 1 to about 15 parts by wt. in one aspect, from about 2 to 10 parts by wt. in another aspect, and from about 3 to 6 parts by wt. in a further aspect of at least one amphiphilic additive (based upon 100 parts by wt. of the monounsaturated monomers utilized to prepare the polymer).

Yield Stress Fluids

In one exemplary aspect of the disclosed technology, the yield stress fluid comprises: i) at least one crosslinked, nonionic amphiphilic polymer(s) described previously; ii) at least one surfactant selected from at least one anionic surfactant, at least one cationic surfactant, at least one amphoteric surfactant, at least one nonionic surfactant, and combinations thereof; and iii) water.

In another exemplary aspect of the disclosed technology, the yield stress fluid comprises: i) at least one crosslinked, nonionic amphiphilic polymer(s) described previously; ii) at least one anionic surfactant; and iii) water.

In another exemplary aspect of the disclosed technology, the yield stress fluid comprises: i) at least one crosslinked, nonionic amphiphilic polymer(s) described previously; ii) at least one anionic surfactant and at least one amphoteric surfactant; and iii) water.

Surprisingly, the present amphiphilic polymers can be activated by a surfactant to provide a stable yield stress fluid with desirable rheological and aesthetic properties with the ability to suspend particulate and insoluble materials in an aqueous medium for indefinite periods of time independent of pH. The yield stress value, elastic modulus and optical clarity are substantially independent of pH in the compositions in which they are included. The yield stress fluid of the disclosed technology is useful in the pH range of from about 2 to about 14 in one aspect, from about 3 to 11 in another aspect, and from about 4 to about 9 in a further aspect. Unlike the pH-responsive crosslinked polymers (acid or base sensitive) that require neutralization with an acid or a base to impart a desired rheological profile, the crosslinked, nonionic, amphiphilic polymers of the rheological profiles of the disclosed technology are substantially independent of pH. By substantially independent of pH is meant that the yield stress fluid within which the polymer of the disclosed technology is included imparts a desired rheological profile (e.g., a yield stress of at least 1 mPa (0.001 Pa) in one aspect, at least at least 0.5 Pa in another aspect, at least 1 Pa in still another aspect, and at least 2 Pa in a further aspect) across a wide pH range (e.g., from about 2 to about 14) wherein the standard deviation in yield stress values across the pH range is less than 1 Pa in one aspect, less than 0.5 Pa in another aspect, and less than 0.25 Pa in a further aspect of the disclosed technology.

In one exemplary aspect of the disclosed technology, the yield stress fluid comprises at least one crosslinked, nonionic, amphiphilic polymer, at least one anionic surfactant, an optional nonionic surfactant, and water.

In another exemplary aspect, the yield stress fluid comprises at least one crosslinked, nonionic amphiphilic polymer, at least one anionic surfactant, at least one amphoteric surfactant, an optional nonionic surfactant, and water.

In still another exemplary aspect, the yield stress fluid comprises at least one crosslinked, nonionic, amphiphilic polymer, at least one anionic ethoxylated surfactant, an optional nonionic surfactant, and water. In one aspect, the average degree of ethoxylation in the anionic surfactant can range from about 1 to about 3. In another aspect, the average degree of ethoxylation is about 2.

In a further exemplary aspect, the yield stress fluid comprises at least one crosslinked, nonionic, amphiphilic polymer, at least one anionic ethoxylated surfactant, at least one amphoteric surfactant, an optional nonionic surfactant, and water. In one aspect, the average degree of ethoxylation in the anionic surfactant can range from about 1 to about 3. In another aspect, the average degree of ethoxylation is about 2.

In a still further exemplary aspect, the yield stress fluid comprises at least one crosslinked, nonionic, amphiphilic polymer, at least one anionic non-ethoxylated surfactant, at least one anionic ethoxylated surfactant, an optional nonionic surfactant, and water. In one aspect, the average degree of ethoxylation in the anionic surfactant can range from about 1 to about 3. In another aspect, the average degree of ethoxylation is about 2.

In another exemplary aspect, the yield stress fluid comprises at least one crosslinked, nonionic, amphiphilic polymer, at least one anionic non-ethoxylated surfactant, at least one anionic ethoxylated surfactant, at least one amphoteric surfactant, an optional nonionic surfactant, and water. In one aspect, the average degree of ethoxylation in the anionic surfactant can range from about 1 to about 3. In another aspect, the average degree of ethoxylation is about 2.

The amount of amphiphilic polymer utilized in formulating the yield stress fluid of the disclosed technology ranges from about 0.5 to about 5 wt. % polymer solids (100% active polymer) based on the weight of the total composition. In another aspect, the amount of amphiphilic polymer utilized in the formulation ranges from about 0.75 wt. % to about 3.5 wt. %. In still another aspect, the amount of amphiphilic polymer employed in the yield stress fluid ranges from about 1 to about 3 wt. %. In a further aspect, the amount of amphiphilic polymer employed in the yield stress fluid ranges from about 1.5 wt. % to about 2.75 wt. %. In a still further aspect, the amount of amphiphilic polymer utilized in the yield stress fluid ranges from about 2 to about 2.5 wt. %. The crosslinked, nonionic, amphiphilic polymer utilized in formulating the yield stress fluids of the disclosed technology is an emulsion polymer.

The yield stress fluids can be prepared by adding an activating surfactant. The activating surfactants utilized to formulate the yield stress fluids of the disclosed technology can be selected from anionic surfactants, cationic surfactants, amphoteric surfactants, nonionic surfactants, and mixtures thereof. The term "activating surfactant" is employed in the context of surfactants employed to activate the amphiphilic polymer to create the yield stress fluid. Some activating surfactants may also be stabilizing surfactants. Various non-limiting examples of activating surfactants are presented below.

Non-limiting examples of anionic surfactants are disclosed in *McCutcheon's Detergents and Emulsifiers*, North American Edition, 1998, published by Allured Publishing Corporation; and McCutcheon's, *Functional Materials*, North American Edition (1992); both of which are incorporated by reference herein in their entirety. The anionic surfactant can be any of the anionic surfactants known or previously used in the art of aqueous surfactant compositions. Suitable anionic surfactants include but are not limited to alkyl sulfates, alkyl ether sulfates, alkyl sulphonates, alkaryl sulfonates, α-olefin-sulphonates, alkylamide sulphonates, alkarylpolyether sulphates, alkylamidoether sulphates, alkyl monoglyceryl ether sulfates, alkyl monoglyceride sulfates, alkyl monoglyceride sulfonates, alkyl succinates, alkyl sulfosuccinates, alkyl sulfosuccinamates, alkyl ether sulphosuccinates, alkyl amidosulfosuccinates; alkyl sulphoacetates, alkyl phosphates, alkyl ether phosphates, alkyl ether carboxylates, alkyl amidoethercarboxylates, N-alkylamino acids, N-acyl amino acids, alkyl peptides, N-acyl taurates, alkyl isethionates, carboxylate salts wherein the acyl group is derived from fatty acids; and the alkali metal, alkaline earth metal, ammonium, amine, and triethanolamine salts thereof.

In one aspect, the cation moiety of the forgoing salts is selected from sodium, potassium, magnesium, ammonium, mono-, di- and triethanolamine salts, and mono-, di-, and tri-isopropylamine salts. The alkyl and acyl groups of the foregoing surfactants contain from about 6 to about 24 carbon atoms in one aspect, from 8 to 22 carbon atoms in another aspect and from about 12 to 18 carbon atoms in a further aspect and can be saturated or unsaturated. The aryl groups in the surfactants are selected from phenyl or benzyl.

The ether containing surfactants set forth above can contain from 1 to 10 ethylene oxide and/or propylene oxide units per surfactant molecule in one aspect, and from 1 to 3 ethylene oxide units per surfactant molecule in another aspect.

Examples of suitable anionic surfactants include but are not limited to the sodium, potassium, lithium, magnesium, and ammonium salts of laureth sulfate, trideceth sulfate, myreth sulfate, $C_{12}$-$C_{13}$ pareth sulfate, $C_{12}$-$C_{14}$ pareth sulfate, and $C_{12}$-$C_{15}$ pareth sulfate, ethoxylated with 1, 2, 3, 4 or 5 moles of ethylene oxide; sodium, potassium, lithium, magnesium, ammonium, and triethanolamine lauryl sulfate, coco sulfate, tridecyl sulfate, myrstyl sulfate, cetyl sulfate, cetearyl sulfate, stearyl sulfate, oleyl sulfate, and tallow sulfate, disodium lauryl sulfosuccinate, disodium laureth sulfosuccinate, sodium cocoyl isethionate, sodium $C_{12}$-$C_{14}$ olefin sulfonate, sodium laureth-6 carboxylate, sodium methyl cocoyl taurate, sodium cocoyl glycinate, sodium myristyl sarcocinate, sodium dodecylbenzene sulfonate, sodium cocoyl sarcosinate, sodium cocoyl glutamate, potassium myristoyl glutamate, triethanolamine monolauryl phosphate, and fatty acid soaps, including the sodium, potassium, ammonium, and triethanolamine salts of a saturated and unsaturated fatty acids containing from about 8 to about 22 carbon atoms.

The cationic surfactants can be any of the cationic surfactants known or previously used in the art of aqueous surfactant compositions. Useful cationic surfactants can be one or more of those described, for example, in *McCutcheon's Detergents and Emulsifiers*, North American Edition, 1998, supra, and Kirk-Othmer, *Encyclopedia of Chemical Technology*, 4th Ed., Vol. 23, pp. 478-541, the contents of which are herein incorporated by reference. Suitable classes of cationic surfactants include but are not limited to alkyl amines, alkyl imidazolines, ethoxylated amines, quaternary compounds, and quaternized esters. In addition, alkyl amine oxides can function as a cationic surfactant at a low pH.

Alkylamine surfactants can be salts of primary, secondary and tertiary fatty $C_{12}$-$C_{22}$ alkylamines, substituted or unsubstituted, and substances sometimes referred to as "amidoamines". Non-limiting examples of alkylamines and salts thereof include dimethyl cocamine, dimethyl palmitamine, dioctylamine, dimethyl stearamine, dimethyl soyamine, soyamine, myristyl amine, tridecyl amine, ethyl stearylamine, N-tallowpropane diamine, ethoxylated stearylamine, dihydroxy ethyl stearylamine, arachidylbehenylamine, dimethyl lauramine, stearylamine hydrochloride, soyamine chloride, stearylamine formate, N-tallowpropane diamine dichloride, and amodimethicone.

Non-limiting examples of amidoamines and salts thereof include stearamido propyl dimethyl amine, stearamidopropyl dimethylamine citrate, palmitamidopropyl diethylamine, and cocamidopropyl dimethylamine lactate.

Non-limiting examples of alkyl imidazoline surfactants include alkyl hydroxyethyl imidazoline, such as stearyl hydroxyethyl imidazoline, coco hydroxyethyl imidazoline, ethyl hydroxymethyl oleyl oxazoline, and the like.

Non-limiting examples of ethyoxylated amines include PEG-cocopolyamine, PEG-15 tallow amine, quaternium-52, and the like.

Among the quaternary ammonium compounds useful as cationic surfactants, some correspond to the general formula: $(R^{20}R^{21}R^{22}R^{23}N^+)E^-$, wherein $R^{20}$, $R^{21}$, $R^{22}$, and $R^{23}$ are independently selected from an aliphatic group having from 1 to about 22 carbon atoms, or an aromatic, alkoxy, polyoxyalkylene, alkylamido, hydroxyalkyl, aryl or alkylaryl group having 1 to about 22 carbon atoms in the alkyl chain; and $E^-$ is a salt-forming anion such as those selected from halogen, (e.g., chloride, bromide), acetate, citrate, lactate, glycolate, phosphate, nitrate, sulfate, and alkylsulfate. The aliphatic groups can contain, in addition to carbon and hydrogen atoms, ether linkages, ester linkages, and other groups such as amino groups. The longer chain aliphatic groups, e.g., those of about 12 carbons, or higher, can be saturated or unsaturated. In one aspect, the aryl groups are selected from phenyl and benzyl.

Exemplary quaternary ammonium surfactants include, but are not limited to cetyl trimethylammonium chloride, cetylpyridinium chloride, dicetyl dimethyl ammonium chloride, dihexadecyl dimethyl ammonium chloride, stearyl dimethyl benzyl ammonium chloride, dioctadecyl dimethyl ammonium chloride, dieicosyl dimethyl ammonium chloride, didocosyl dimethyl ammonium chloride, dihexadecyl dimethyl ammonium chloride, dihexadecyl dimethyl ammonium acetate, behenyl trimethyl ammonium chloride, benzalkonium chloride, benzethonium chloride, and di(coco-nutalkyl) dimethyl ammonium chloride, ditallowdimethyl ammonium chloride, di(hydrogenated tallow) dimethyl ammonium chloride, di(hydrogenated tallow) dimethyl ammonium acetate, ditallowdimethyl ammonium methyl sulfate, ditallow dipropyl ammonium phosphate, and ditallow dimethyl ammonium nitrate.

At low pH, amine oxides can protonate and behave similarly to N-alkyl amines. Examples include, but are not limited to, dimethyl-dodecylamine oxide, oleyldi(2-hydroxyethyl) amine oxide, dimethyltetradecylamine oxide, di(2-hydroxyethyl)-tetradecylamine oxide, dimethylhexadecylamine oxide, behenamine oxide, cocamine oxide, decyltetradecylamine oxide, dihydroxyethyl $C_{12}$-$C_{15}$ alkoxypropylamine oxide, dihydroxyethyl cocamine oxide, dihydroxyethyl lauramine oxide, dihydroxyethyl stearamine oxide, dihydroxyethyl tallowamine oxide, hydrogenated palm kernel amine oxide, hydrogenated tallowamine oxide, hydroxyethyl hydroxypropyl $C_{12}$-$C_{15}$ alkoxypropylamine oxide, lauramine oxide, myristamine oxide, cetylamine oxide, oleamidopropylamine oxide, oleamine oxide, palmitamine oxide, PEG-3 lauramine oxide, dimethyl lauramine oxide, potassium trisphosphonomethylamine oxide, soyamidopropylamine oxide, cocamidopropylamine oxide, stearamine oxide, tallowamine oxide, and mixtures thereof.

The term "amphoteric surfactant" as used herein, is also intended to encompass zwitterionic surfactants, which are well known to formulators skilled in the art as a subset of amphoteric surfactants. Nonlimiting examples of amphoteric surfactants are disclosed *McCutcheon's Detergents and Emulsifiers*, North American Edition, supra, and McCutcheon's, *Functional Materials*, North American Edition, supra; both of which are incorporated by reference herein in their entirety. Suitable examples include but are not limited to amino acids (e.g., N-alkyl amino acids and N-acyl amino acids), betaines, sultaines, and alkyl am phocarboxylates.

Amino acid based surfactants suitable in the practice of the disclosed technology include surfactants represented by the formula:

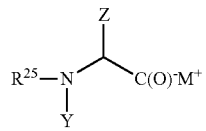

wherein $R^{25}$ represents a saturated or unsaturated hydrocarbon group having 10 to 22 carbon atoms or an acyl group containing a saturated or unsaturated hydrocarbon group having 9 to 22 carbon atoms, Y is hydrogen or methyl, Z is selected from hydrogen, —$CH_3$, —$CH(CH_3)_2$, —$CH_2CH(CH_3)_2$, —$CH(CH_3)CH_2CH_3$, —$CH_2C_6H_5$, —$CH_2C_6H_4OH$, —$CH_2OH$, —$CH(OH)CH_3$, —$(CH_2)_4NH_2$, —$(CH_2)_3NHC(NH)NH_2$, —$CH_2C(O)O\text{-}M^+$, —$(CH_2)_2 C(O)O\text{-}M^+$. M is a salt forming cation. In one aspect, $R^{25}$ represents a radical selected from a linear or branched $C_{10}$ to $C_{22}$ alkyl group, a linear or branched $C_{10}$ to $C_{22}$ alkenyl group, an acyl group represented by $R^{26}C(O)$—, wherein $R^{26}$ is selected from a linear or branched $C_9$ to $C_{22}$ alkyl group, a linear or branched $C_9$ to $C_{22}$ alkenyl group. In one aspect, $M^+$ is a cation selected from sodium, potassium, ammonium, and triethanolamine (TEA).

The amino acid surfactants can be derived from the alkylation and acylation of α-amino acids such as, for example, alanine, arginine, aspartic acid, glutamic acid, glycine, isoleucine, leucine, lysine, phenylalanine, serine, tyrosine, and valine. Representative N-acyl amino acid surfactants are, but not limited to the mono- and di-carboxylate salts (e.g., sodium, potassium, ammonium and TEA) of N-acylated glutamic acid, for example, sodium cocoyl glutamate, sodium lauroyl glutamate, sodium myristoyl glutamate, sodium palmitoyl glutamate, sodium stearoyl glutamate, disodium cocoyl glutamate, disodium stearoyl glutamate, potassium cocoyl glutamate, potassium lauroyl glutamate, and potassium myristoyl glutamate; the carboxylate salts (e.g., sodium, potassium, ammonium and TEA) of N-acylated alanine, for example, sodium cocoyl alaninate, and TEA lauroyl alaninate; the carboxylate salts (e.g., sodium, potassium, ammonium and TEA) of N-acylated glycine, for example, sodium cocoyl glycinate, and potassium cocoyl glycinate; the carboxylate salts (e.g., sodium, potassium, ammonium and TEA) of N-acylated sarcosine, for example, sodium lauroyl sarcosinate, sodium cocoyl sarcosinate, sodium myristoyl sarcosinate, sodium oleoyl sarcosinate, and ammonium lauroyl sarcosinate; and mixtures of the foregoing surfactants.

The betaines and sultaines useful in the disclosed technology are selected from alkyl betaines, alkylamino betaines, and alkylamido betaines, as well as the corresponding sulfobetaines (sultaines) represented by the formulas:

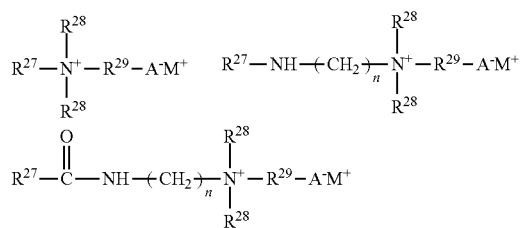

wherein $R^{27}$ is a $C_7$-$C_{22}$ alkyl or alkenyl group, each $R^{28}$ independently is a $C_1$-$C_4$ alkyl group, $R^{29}$ is a $C_1$-$C_5$ alkylene group or a hydroxy substituted $C_1$-$C_5$ alkylene group, n is an integer from 2 to 6, A is a carboxylate or sulfonate group, and M is a salt forming cation. In one aspect, $R^{27}$ is a $C_{11}$-$C_{18}$ alkyl group or a $C_{11}$-$C_{18}$ alkenyl group. In one aspect, $R^{28}$ is methyl. In one aspect, $R^{29}$ is methylene, ethylene or hydroxy propylene. In one aspect, n is 3. In a further aspect, M is selected from sodium, potassium, magnesium, ammonium, and mono-, di- and triethanolamine cations.

Examples of suitable betaines include, but are not limited to, lauryl betaine, coco betaine, oleyl betaine, cocohexadecyl dimethylbetaine, lauryl amidopropyl betaine, cocoamidopropyl betaine (CAPB), and cocamidopropyl hydroxysultaine.

The alkylamphocarboxylates such as the alkylamphoacetates and alkylamphopropionates (mono- and disubstituted carboxylates) can be represented by the formula:

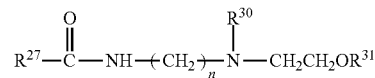

wherein $R^{27}$ is a $C_7$-$C_{22}$ alkyl or alkenyl group, $R^{30}$ is —$CH_2C(O)O^-$ $M^+$, —$CH_2CH_2C(O)O^-$ $M^+$, or —$CH_2CH(OH)CH_2SO_3^-$ $M^+$, $R^{31}$ is hydrogen or —$CH_2C(O)O\text{-}M^+$, and M is a cation selected from sodium, potassium, magnesium, ammonium, and mono-, di- and triethanolamine.

Exemplary alkylamphocarboxylates include, but are not limited to, sodium cocoamphoacetate, sodium lauroamphoacetate, sodium capryloamphoacetate, disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, and disodium capryloamphodipropionate.

Non-limiting examples of nonionic surfactants are disclosed in *McCutcheon's Detergents and Emulsifiers*, North American Edition, 1998, supra; and McCutcheon's, *Functional Materials*, North American, supra; both of which are incorporated by reference herein in their entirety. Additional Examples of nonionic surfactants are described in U.S. Pat. No. 4,285,841, to Barrat et al., and U.S. Pat. No. 4,284,532, to Leikhim et al., both of which are incorporated by reference herein in their entirety. Nonionic surfactants typically have a hydrophobic portion, such as a long chain alkyl group or an alkylated aryl group, and a hydrophilic portion containing various degrees of ethoxylation and/or propoxylation (e.g., 1 to about 50) ethoxy and/or propoxy moieties. Examples of some classes of nonionic surfactants that can be used include, but are not limited to, ethoxylated alkylphenols, ethoxylated and propoxylated fatty alcohols, polyethylene glycol ethers of methyl glucose, polyethylene glycol ethers of sorbitol, ethylene oxide-propylene oxide block copolymers, ethoxylated esters of fatty acids, condensation products of ethylene oxide with long chain amines or amides, condensation products of ethylene oxide with alcohols, and mixtures thereof.

Suitable nonionic surfactants include, for example, alkyl polysaccharides, alcohol ethoxylates, block copolymers, castor oil ethoxylates, ceto/oleyl alcohol ethoxylates, cetearyl alcohol ethoxylates, decyl alcohol ethoxylates, dinonyl phenol ethoxylates, dodecyl phenol ethoxylates, end-capped ethoxylates, ether amine derivatives, ethoxylated alkanolam ides, ethylene glycol esters, fatty acid alkanolam ides, fatty alcohol alkoxylates, lauryl alcohol ethoxylates, monobranched alcohol ethoxylates, nonyl phenol ethoxylates, octyl phenol ethoxylates, oleyl amine ethoxylates, random copolymer alkoxylates, sorbitan ester ethoxylates, stearic acid ethoxylates, stearyl amine ethoxylates, tallow oil fatty acid ethoxylates, tallow amine ethoxylates, tridecanol ethoxylates, acetylenic diols, polyoxyethylene sorbitols, and mixtures thereof. Various specific examples of suitable nonionic surfactants include, but are not limited to, methyl gluceth-10, PEG-20 methyl glucose distearate, PEG-20 methyl glucose sesquistearate, ceteth-8, ceteth-12, dodoxynol-12, laureth-15, PEG-20 castor oil, polysorbate 20, steareth-20, polyoxyethylene-10 cetyl ether, polyoxyethylene-10 stearyl ether, polyoxyethylene-20 cetyl ether, polyoxyethylene-10 oleyl ether, polyoxyethylene-20 oleyl ether, an ethoxylated nonylphenol, ethoxylated octylphenol, ethoxylated dodecylphenol, or ethoxylated fatty ($C_6$-$C_{22}$) alcohol, including 3 to 20 ethylene oxide moieties, polyoxyethylene-20 isohexadecyl ether, polyoxyethylene-23 glycerol laurate, polyoxyethylene-20 glyceryl stearate, PPG-10 methyl glucose ether, PPG-20 methyl glucose ether, polyoxyethylene-20 sorbitan monoesters, polyoxyethylene-80 castor oil, polyoxyethylene-15 tridecyl ether, polyoxyethylene-6 tridecyl ether, laureth-2, laureth-3, laureth-4, PEG-3 castor oil, PEG 600 dioleate, PEG 400 dioleate, poloxamers such as poloxamer 188, polysorbate 21, polysorbate 40, polysorbate 60, polysorbate 61, polysorbate 65, polysorbate 80, polysorbate 81, polysorbate 85, sorbitan caprylate, sorbitan cocoate, sorbitan diisostearate, sorbitan dioleate, sorbitan distearate, sorbitan fatty acid ester, sorbitan isostearate, sorbitan laurate, sorbitan oleate, sorbitan palmitate, sorbitan sesquiisostearate, sorbitan sesquioleate, sorbitan sesquistearate, sorbitan stearate, sorbitan triisostearate, sorbitan trioleate, sorbitan tristearate, sorbitan undecylenate, or mixtures thereof.

Alkyl glycoside nonionic surfactants can also be employed and are generally prepared by reacting a monosaccharide, or a compound hydrolyzable to a monosaccharide, with an alcohol such as a fatty alcohol in an acid medium. For example, U.S. Pat. Nos. 5,527,892 and 5,770,543 describe alkyl glycosides and/or methods for their preparation. Suitable examples are commercially available under the names of Glucopon™ 220, 225, 425, 600 and 625, PLANTACARE®, and PLANTAPON®, all of which are available from Cognis Corporation of Ambler, Pa.

In another aspect, nonionic surfactants include, but are not limited to, alkoxylated methyl glucosides such as, for example, methyl gluceth-10, methyl gluceth-20, PPG-10 methyl glucose ether, and PPG-20 methyl glucose ether, available from Lubrizol Advanced Materials, Inc., under the trade names, Glucam® E10, Glucam® E20, Glucam® P10, and Glucam® P20, respectively; and hydrophobically modified alkoxylated methyl glucosides, such as PEG 120 methyl glucose dioleate, PEG-120 methyl glucose trioleate, and PEG-20 methyl glucose sesquistearate, available from Lubrizol Advanced Materials, Inc., under the trade names, Glucamate® DOE-120, Glucamate™ LT, and Glucamate™ SSE-20, respectively, are also suitable. Other exemplary hydrophobically modified alkoxylated methyl glucosides are disclosed in U.S. Pat. Nos. 6,573,375 and 6,727,357, the disclosures of which are hereby incorporated by reference in their entirety.

Other useful nonionic surfactants include water soluble silicones such as PEG-10 Dimethicone, PEG-12 Dimethicone, PEG-14 Dimethicone, PEG-17 Dimethicone, PPG-12 Dimethicone, PPG-17 Dimethicone and derivatized/functionalized forms thereof such as Bis-PEG/PPG-20/20 Dimethicone Bis-PEG/PPG-16/16 PEG-PPG-16/16 Dimethicone, PEG/PPG-14/4 Dimethicone, PEG/PPG-20/20 Dimethicone, PEG/PPG-20/23 Dimethicone, and Perfluorononylethyl Carboxydecyl PEG-10 Dimethicone.

The amount of the at least one surfactant (active weight basis) utilized in formulating the yield stress fluid of the disclosed technology ranges from about 1 to about 70 wt. % based on the weight of the total yield stress fluid composition. In another aspect, the amount of the at least one surfactant utilized in the formulation ranges from about 2 to about 50 wt. % or from about 3 to about 25 wt. %. In still another aspect, the amount of the at least one surfactant employed in the yield stress fluid ranges from about 5 to about 22 wt. %. In a further aspect, the amount of the at least one surfactant utilized ranges from about 6 to about 20 wt. %. In still a further aspect, the amount of at least one surfactant is about 10, 12, 14, 16, and 18 wt. % based on the total weight yield of the stress fluid.

In one embodiment of the disclosed technology, the weight ratio (based on active material) of anionic surfactant (non-ethoxylated and/or ethoxylated) to amphoteric surfactant can range from about 10:1 to about 2:1 in one aspect, and can be 9:1, 8:1, 7:1 6:1, 5:1, 4.5:1, 4:1, or 3:1 in another aspect. When employing an ethoxylated anionic surfactant in combination with a non-ethoxylated anionic surfactant and an amphoteric surfactant, the weight ratio (based on active material) of ethoxylated anionic surfactant to non-ethoxylated anionic surfactant to amphoteric surfactant can range from about 3.5:3.5:1 in one aspect to about 1:1:1 in another aspect.

In one embodiment, the yield stress value of the fluid is at least about 1 mPa, or 0.1 Pa in one aspect, about 0.5 Pa in one aspect, at least about 1 Pa in another aspect and at least about 1.5 Pa in a further aspect. In another embodiment, the yield stress of the fluid ranges from about 0.1 to about 20 Pa in one aspect, from about 0.5 Pa to about 10 Pa in another aspect, from about 1 to about 3 Pa in a further aspect, and from about 1.5 to about 3.5 in a still further aspect.

Optionally, the yield stress fluids of the disclosed technology can contain an electrolyte. Suitable electrolytes are known compounds and include organic and inorganic salts of multivalent anions, such as potassium pyrophosphate, potassium tripolyphosphate, and sodium or potassium citrate, salts of multivalent cations, including alkaline earth metal salts such as calcium chloride and calcium bromide, as well as zinc halides, barium chloride and calcium nitrate, salts of monovalent cations with monovalent anions, including alkali metal or ammonium halides, such as potassium chloride, sodium chloride, potassium iodide, sodium bromide, and ammonium bromide, alkali metal or ammonium nitrates, and blends thereof.

The amount of the electrolyte used will generally depend on the amount of the amphiphilic polymer incorporated, but may be used at concentration levels of from about 0.1 to about 4 wt. % in one aspect and from about 0.2 to about 3 wt. % in another aspect, from about 0.5 to about 2.5 in a further aspect, and from about 0.75 to about 1.5 wt. % in a still further aspect, based on the weight of the total composition.

Optionally, the yield stress fluids of the disclosed technology can contain organic acid preservatives and salts thereof. Any acid based preservative that is useful in personal care, home care, health care, and institutional and industrial care products can be used in the compositions of the present invention. In one aspect the acid preservative is a carboxylic acid compound represented by the formula: $R^{40}C(O)OH$, wherein $R^{40}$ represents hydrogen, a saturated and unsaturated hydrocarbyl group containing 1 to 8 carbon atoms or $C_6$ to $C_{10}$ aryl. In another aspect, $R^{40}$ is selected from a hydrogen, a $C_1$ to $C_8$ alkyl group, a $C_2$ to $C_8$ alkenyl group, or phenyl. Exemplary acids are, but are not limited to, formic acid, acetic acid, propionic acid, sorbic acid, caprylic acid, and benzoic acid, and mixtures thereof.

In another aspect, suitable acids include but are not limited to, oxalic acid, succinic acid, glutaric acid, adipic acid, azelaic acid, maleic acid, fumaric acid, lactic acid, glyceric acid, tartronic acid malic acid, tartaric acid, gluconic acid, citric acid, ascorbic acid, salicylic acid, phthalic acid, mandelic acid, benzilic acid, and mixtures thereof.

Salts of the foregoing acids are also useful as long as they retain efficacy at low pH values. Suitable salts include the alkali metal (e.g., sodium, potassium, calcium) and ammonium salts of the acids enumerated above.

The acid based preservatives and/or their salts can be used alone or in combination with non-acidic preservatives typically employed in personal care, homecare, health care, and institutional and industrial care products.

The preservatives typically comprise from about 0.01% to about 3.0% by weight in one aspect, from about 0.1% to about 1% by weight in another aspect, and from about 0.3% to about 1% by weight in a further aspect, of the total weight of the personal care compositions of the present invention.

The yield stress fluid must be easily pourable with a shear thinning index of less than 0.5 at shear rates between 0.1 and 1 reciprocal second. The yield stress fluid can have an optical transmission of at least 10%. In addition, or alternatively, the yield stress fluid can have a nephelometric turbidity unit (NTU) value of 50 or less, or 40 or less, or even 30 or 20 or less. The yield stress fluid of the disclosed technology can be utilized in combination with a rheology modifier (thickener) to enhance the yield value of a thickened liquid. In one aspect, the yield stress fluid of the disclosed technology can be combined with a nonionic rheology modifier which rheology modifier when utilized alone does not have a sufficient yield stress value. Any rheology modifier is suitable, so long as such is soluble in water, stable and contains no ionic or ionizable groups. Suitable rheology modifiers include, but are not limited to natural gums (e.g., polygalactomannan gums selected from fenugreek, cassia, locust bean, tara and guar), modified cellulose (e.g., ethylhexylethylcellulose (EHEC), hydroxybutylmethylcellulose (HBMC), hydroxyethylmethylcellulose (NEMC), hydroxypropylmethylcellulose (HPMC), methyl cellulose (MC), hydroxyethylcellulose (HEC), hydroxypropylcellulose (HPC) and cetyl hydroxyethylcellulose); and mixtures thereof methylcellulose, polyethylene glycols (e.g., PEG 4000, PEG 6000, PEG 8000, PEG 10000, PEG 20000), polyvinyl alcohol, polyacrylamides (homopolymers and copolymers), and hydrophobically modified ethoxylated urethanes (HEUR). The rheology modifier can be utilized in an amount ranging from about 0.5 to about 25 wt. % in one aspect, from about 1 to about 15 wt. % in another aspect, and from about 2 to about 10 wt. % in a further aspect, based on the weight of the total weight of the composition.

The yield stress fluids of the disclosed technology can be used in any application requiring yield stress properties. The yield stress fluids can be used alone or in combination with other fluids to enhance the yield stress values thereof.

In one embodiment, the yield stress fluids of the disclosed technology can be utilized to suspend particulate materials and insoluble droplets within an aqueous composition. Such fluids are useful in the oil and gas, personal care, homecare, coatings and inks and adhesive/binder industries.

In the oil and gas industry, the yield stress fluids of the disclosed technology can be used to enhance the yield stress value of drilling and hydraulic fracturing fluids, and can be employed to suspend borehole cuttings and fracturing proppants such as, for example, sand, sintered bauxite, glass balls, ceramic materials, polystyrene beads, and the like.

In the personal and homecare industries, the yield stress fluids of the disclosed technology can be utilized to improve the yield stress properties of detersive compositions, hair and skin care compositions, as well as cosmetics, and can be utilized to suspend insoluble silicones, opacifiers and pearlescent agents (e.g., mica, coated mica), pigments, exfoliants, anti-dandruff agents, clay, swellable clay, laponite, gas bubbles, liposomes, microsponges, cosmetic beads, perfumes fragrance oils, fragrance microcapsules, fragrance particles, benefit agent containing microcapsules and particles, cosmetic microcapsules, and flakes. The yield stress fluids of the disclosed technology can stabilize these materials in suspension for at least one month at 23° C. in one aspect, at least 6 months in another aspect, and at least one year in a further aspect.

Exemplary perfumes, fragrances and fragrance oils include but are not limited to allyl cyclohexane propionate, ambrettolide, Ambrox® DL (dodecahydro-3a,6,6,9a-tetramethylnaphtho[2,1-b]furan), amyl benzoate, amyl cinnamate, amyl cinnamic aldehyde, amyl salicylate, anethol, aurantiol, benzophenone, benzyl butyrate, benzyl iso-valerate, benzyl salicylate, cadinene, campylcyclohexal, cedrol, cedryl acetate, cinnamyl cinnamate, citronellyl acetate, citronellyl isobutyrate, citronellyl propionate, cuminic aldehyde, cyclohexylsalicylate, cyclamen aldehyde, cyclomyral, dihydro isojasmonate, diphenyl methane, diphenyl oxide, dodecanal, dodecalactone, ethylene brassylate, ethylmethyl phenylglycidate, ethyl undecylenate, exaltolide, Galoxilide® (1,3,4,6,7,8-hexhydro,4,6,6,7,8,8-hexamethyl-cyclopenta-γ-2-benzopyran), geranyl acetate, geranyl isobutyrate, hexadecanolide, hexenyl salicylate, hexyl cinnamic aldehyde, hexyl salicylate, α-ionone, β-ionone, γ-ionone, α-irone, isobutyl benzoate, isobutyl quinoline, Iso E Super® (7-acetyl,1,2,3,4,5,6,7,8-octahydro,1,1,6,7-tetramethyl napthalene), cis-jasmone, lilial, linalyl benzoate, 20 methoxy naphthaline, methyl cinnamate, methyl eugenol, γ-methylionone, methyl linolate, methyl linolenate, musk indanone, musk ketone, musk tibetine, myristicin, neryl acetate, O-nonalactone, γ-nonalactone, patchouli alcohol, phantolide, phenylethyl benzoate, phenylethylphenylacetate, 2-phenylethanol, phenyl heptanol, phenyl hexanol, α-santalol, thibetolide, tonalid, δ-undecalactone, γ-undecalactone, vertenex, vetiveryl acetate, yara-yara, ylangene, allo-ocimene, allyl caproate, allyl heptoate, anisole, camphene, carvacrol, carvone, citral, citronellal, citronellol, citronellyl nitrile, coumarin, cyclohexyl ethylacetate, p-cymene, decanal, dihydromyrcenol, dihydromyrcenyl acetate, dimethyl octanol, ethyllinalool, ethylhexyl ketone, eucalyptol, fenchyl acetate, geraniol, gernyl formate, hexenyl isobutyrate, hexyl acetate, hexyl neopentanoate, heptanal, isobornyl acetate, isoeugenol, isomenthone, isononyl acetate, isononyl alcohol, isomenthol, isopulegol, limonene, linalool, linalyl acetate, menthyl acetate, methyl chavicol, methyl octyl acetaldehyde, myrcene, napthalene, nerol, neral, nonanal, 2-nonanone, nonyl acetate, octanol, octanal, α-pinene, β-pinene, rose oxide, α-terpinene, γ-terpinene, α-terpinenol, terpinolene, terpinyl acetate, tetrahydrolinalool, tetrahydromyrcenol, undecenal, veratrol, verdox, acetanisol; amyl acetate; anisic aldehyde; anisylalcohol; benzaldehyde; benzyl acetate; benzyl acetone; benzyl alcohol; benzyl formate; hexenol; laevo-carveol; d-carvone; cinnamaldehyde; cinnamic alcohol; cinnamyl acetate; cinnamyl formate; cis-3-hexenyl acetate; Cyclal C (2,4-dimethyl-3-cyclohexen-1-carbaldehyde); dihydroxyindole; dimethyl benzyl carbinol; ethyl acetate; ethyl acetoacetate; ethyl butanoate; ethyl butyrate; ethyl vanillin; tricyclo decenyl propionate; furfural; hexanal; hexenol; hydratropic alcohol; hydroxycitronellal; indole; isoamyl alcohol; isopulegyl acetate; isoquinoline; ligustral; linalool oxide; methyl acetophenone; methyl amyl ketone; methyl anthranilate; methyl benzoate; methyl benzyl acetate; methyl heptenone; methyl heptyl ketone; methyl phenyl carbinyl acetate; methyl salicylate; octalactone; para-cresol; para-methoxy acetophenone; para-methyl acetophenone; phenethylalcohol; phenoxy ethanol; phenyl acetaldehyde; phenyl ethyl acetate; phenyl ethyl alcohol; prenyl acetate; propyl butyrate; safrole; vanillin and viridine.

In the coatings, inks, and adhesive/binder industries the yield stress fluids and non-ionic amphiphilic polymer composition with its at least one amphiphilic crosslinking agent can be utilized at a variety of different pH values and are useful to adjust viscosity of a fluid to: a) control or minimize settling or creaming of solid particles, dispersed liquids, trapped gases, and particulates (aid in suspension) that are more dense or less dense than the continuous media (often water based); b) to control application viscosity of continuous or discontinuous layers of a coating, ink, or adhesive to a substrate; c) to minimize movement or flow of coatings, inks, or adhesives immediately prior to application or in the time after application until the coating, ink, or adhesive forms a continuous gelled polymer; e) reduce splatter and misting in some application processes; f) etc., to facilitate optimal storage, application ease, and final surface finish in those applications. The coatings, inks and adhesives may comprise particulate or fibrous fillers, pigments, dyes, other polymers, surfactants and/or dispersants, coalescents, plasticizers, biocides and other conventional additives employed in coatings, inks, and adhesives. The coatings can be used on metals, plastics, wood, masonry, textiles, papers, etc. The inks can be used on any ink substrates such as paper, polymers, wovens, nonwovens, films, etc. The amphiphilic polymer can contribute to both viscosity control and optical clarity (helping color intensity of pigmented compositions) of the coating, ink, or adhesive.

The stable compositions maintain a smooth, acceptable rheology with good shear thinning properties without significant increases or decreases in viscosity, with no phase separation, e.g., settling or creaming out (rising to the surface), or loss of clarity over extended periods of time, such as for at least one month at 45° C.

Exemplary bead components include, but are not limited to, agar beads, alginate beads, jojoba beads, gelatin beads, Styrofoam™ beads, polyacrylate, polymethylmethacrylate (PMMA), polyethylene beads, Unispheres™ and Unipearls™ cosmetic beads (Induchem USA, Inc., New York, N.Y.), Lipocapsule™, Liposphere™, and Lipopearl™ microcapsules (Lipo Technologies Inc., Vandalia, Ohio), and Confetti II™ dermal delivery flakes (United-Guardian, Inc., Hauppauge, N.Y.). Beads can be utilized as aesthetic materials or can be used to encapsulate benefit agents to protect them from the deteriorating effects of the environment or for optimal delivery, release and performance in the final product.

In one aspect, the cosmetic beads range in size from about 0.5 to about 1.5 mm. In another aspect, the difference in specific gravity of the bead and water is between about +/−0.01 and 0.5 in one aspect and from about +/−0.2 to 0.3 g/ml in another aspect.

In one aspect, the microcapsules range in size from about 0.5 to about 300 μm. In another aspect, the difference in specific gravity between the microcapsules and water is from about +/−0.01 to 0.5. Non-limiting examples of microcapsule beads are disclosed in U.S. Pat. No. 7,786,027, the disclosure of which is herein incorporated by reference.

In one aspect of the disclosed technology, the amount of particulate component and/or insoluble droplets can range from about 0.1% to about 10% by weight based on the total weight of the composition.

While overlapping weight ranges for the various components and ingredients that can be contained in the yield stress fluids of the disclosed technology have been expressed for selected embodiments and aspects of the disclosed technology, it should be readily apparent that the specific amount of each component in the compositions will be selected from its disclosed range such that the amount of each component is adjusted so that the sum of all components in the composition will total 100 weight percent. The amounts employed will vary with the purpose and character of the desired product and can be readily determined by one skilled in the formulation art and from the literature.

The disclosed technology is illustrated by the following examples that are merely for the purpose of illustration and are not to be regarded as limiting the scope of the disclosed technology or the manner in which it can be practiced. Unless specifically indicated otherwise, parts and percentages are given by weight.

Test Methodology
Yield Stress

The yield stress values of the polymers are determined by oscillatory and steady shear measurements on a controlled stress rheometer (TA Instruments Discovery HR-2 rheometer, New Castle, Del.) utilizing parallel plate geometry (40 mm 2° cone-plate geometry) at 25° C. The oscillatory measurements are performed at a fixed frequency of 1 rad/sec. The elastic and viscous moduli (G' and G" respectively) are obtained as a function of increasing stress amplitude. The stress corresponding to the crossover of G' and G" is noted as the yield stress.

Brookfield Viscosity

Brookfield rotating spindle method (all viscosity measurements reported herein are conducted by the Brookfield method whether mentioned or not): The viscosity measurements are calculated in mPa·s, employing a Brookfield rotating spindle viscometer, Model RVT (Brookfield Engineering Laboratories, Inc.), at about 20 revolutions per minute (rpm), at ambient room temperature of about 20 to 25° C. (BV viscosity). Spindle sizes are selected in accordance with the standard operating recommendations from the manufacturer. Generally, spindle sizes are selected as follows:

| Spindle Size No. | Viscosity Range (mPa · s) |
| --- | --- |
| 1 | 1-50 |
| 2 | 500-1,000 |
| 3 | 1,000-5,000 |
| 4 | 5,000-10,000 |
| 5 | 10,000-20,000 |
| 6 | 20,000-50,000 |
| 7 | >50,000 |

The spindle size recommendations are for illustrative purposes only. The artisan of ordinary skill in the art will select a spindle size appropriate for the system to be measured. A no. 4 or 5 spindle was utilized for the viscosity measurements herein.

Bead Suspension Test

The ability of a polymer system to suspend active and/or aesthetically pleasing insoluble oily and particulate materials is important from the standpoint of product efficacy and appeal. A six dram vial (approximately 70 mm high×25 mm in diameter) is filled to the 50 mm point with the test formulation. Each sample vial is centrifuged to remove any trapped air bubbles contained in the formulation. Approximately 0.1 of equal portions (by wt.) of mixed beads Lipopearls DS5293 beads (particle size=300-3000 μm) (commercially available from Lipo Technologies) and Unispheres™ NTL-2512 beads (particle size=1000-1500 μm) and NTL-2103 beads (particle size=500-900 μm) (commercially available from InduChem AG) are added to each sample vial and are stirred gently with a wooden stick until they are uniformly dispersed throughout the sample. The mixture of beads of various sizes allows for a full assessment of the suspension ability of a polymer system. The position of the beads within each sample vial is noted by taking a photograph immediately after preparation to establish the initial position of the beads within the formulation. The vials are oven aged at 40 to 50° C. for a period ranging from 6 weeks to 3 months. The bead suspension properties of each sample are visually evaluated at the conclusion of the 6 or 12 week test period. If the initial position of all of the beads is unchanged following the conclusion of the test period the sample passes. If the initial position of one or more of the beads changes (or the beads cream to the top and/or settle to the bottom of the vial) following the conclusion of the test period the sample fails.

Light Transmittance (Optical Clarity)

The optical clarity (expressed as percent transmittance or % T) of a test composition is measured in % T (transmittance) by a Shimadzu 3600 UV-visible-NIR spectrophotometer from a wavelength of 800 nm to 300 nm at ambient room temperature of about 20 to 25° C. A 4 mL PMMA cuvette cell is filled almost to the top with test sample and centrifuged at 1400 rpm until all bubbles are removed. Upon centrifugation, each sample vial is wiped with tissue paper to remove any smudges before placement in the spectrophotometer. Clarity measurements are taken against deionized water (clarity rating of 100%). Compositions having a clarity value of about 70% (T) or more at the low wavelength of 400 nm are substantially clear. Compositions having a clarity value in the range of about 45 to 69% (T) are substantially translucent. Compositions having a clarity value of 80% and above are considered clear.

Turbidity

The turbidity (cloudiness or haziness) of a composition is determined in Nephelometric Turbidity Units (NTU) employing a nephelometric turbidity meter (Mircro 100 Turbidimeter, HF Scientific, Inc.) at ambient room temperature of about 20 to 25° C. Distilled water (NTU=0) is utilized as a standard. Six dram screw cap vials (70 mm×25 mm) are filled almost to the top with test sample and centrifuged at 2200 rpm until all bubbles are removed. Upon centrifugation, each sample vial is wiped with tissue paper to remove any smudges before placement in the turbidity meter. The sample is placed in the turbidity meter and a reading is taken. Once the reading stabilizes the NTU value is recorded. The vial is given one-quarter turn and another reading is taken and recorded. This is repeated until four readings are taken. The lowest of the four readings is reported as the turbidity value. Lower turbidity values indicate clearer (less turbid) compositions.

Diffuse Reflection Test

Diffuse reflection is the reflection of light from a surface such that an incident ray is reflected at many angles rather than at just one angle as in the case of specular reflection. It is diffusely-scattered light that forms the image of the object in the observer's eye. To quantify the intensity of the structural color of polymer formulation, diffuse reflection is measured by a Shimadzu 3600 UV-visible-NIR spectrophotometer using a Shimadzu ISR-3100 60 mm integrating sphere. Tested polymers are formulated with the components of Formula A. A 4 mL PMMA cuvette cell is filled almost to the top with test sample and centrifuged at 1400 rpm until all bubbles are removed. Upon centrifugation, each sample vial is wiped with tissue paper to remove any smudges before placement in the spectrophotometer. Percent Reflectance (y-axis) is plotted against wavelength, nm (x-axis). Lower reflectance peaks are indicative of clearer compositions.

Latex Polymer Particle Size

The average particle size of the latex polymer particles is measured by the standard dynamic light scattering (DLS) technique utilizing a Zetasizer Nano ZS™ DLS instrument (Malvern Instruments Inc.). A dilute dispersion of polymer latex (0.03 wt %) in deionized water is prepared and measured via DLS at 25° C.

The following abbreviations and trade names are utilized in the examples.

| Ingredient Descriptions and Abbreviations | |
|---|---|
| AM (E-Sperse ® RS-1618) | Amphiphilic crosslinker with two polymerizable reactive groups from Ethox Chemical, LLC |
| BEM | Sipomer ® Polyethoxylated (25 moles) Behenyl Methacrylate (66.67% BEM/33.33% MAA by wt.), Rhodia |
| CAPB | Chembetaine ™ CAD, Cocamidopropyl Betaine (amphoteric surfactant), Lubrizol Advanced Materials, Inc. (35% active) |
| DI Water | Deionized Water |
| Ethoxylated MEG Ester (EMegE) | Glucamate ™ VLT Liquid Thickener, INCI: PEG-120 Methyl Glucose Trioleate (and) Propanediol (68-72% active), Lubrizol Advanced Materials, Inc. |
| Ethoxylated MEG Ester (EMegE) | Glucamate ™ LT Liquid Thickener, INCI: PEG-120 Methyl Glucose Trioleate (and) Propylene Glycol and (Water) (37-43% active), Lubrizol Advanced Materials, Inc. |
| Ethoxylated MEG Ester (EMegE) | Glucamate ™ DOE-120 Solid Thickener, INCI: PEG-120 Methyl Glucose Dioleate, Lubrizol Advanced Materials, Inc. |
| EA | Ethyl Acrylate |
| HEMA | 2-Hydroxyethyl Methacrylate |
| n-BA | n-Butyl Acrylate |
| PPG-PEG-PPG Block Copolymer | Pluronic ™ 10R5 Polypropylene glycol)-block-poly(ethylene glycol)-block-poly(propylene glycol) copolymer; $M_n \approx 2{,}000$; PEG $\approx$ 50 wt. %, purchased from Sigma-Aldrich |
| Poly(ethylene glycol-4000) dioleate | Mulsifan 4000 DO PEG (90) Dioleate, Zschimmer & Schwarz Incorporated |
| Poly(ethylene glycol-1000) dioleate | Mulsifan 1000 DO PEG (23) Dioleate, Zschimmer & Schwarz Incorporated |
| Poly(ethylene glycol-600) distearate | Mulsifan 600 DS PEG (14) Distearate, Zschimmer & Schwarz Incorporated |
| Poly(ethylene glycol-600) dioleate | Mulsifan 600 DO PEG (14) Dioleate, Zschimmer & Schwarz Incorporated |
| Polyquaternium-7 | Merquat ™ 7SPR polymer, Lubrizol Advanced Materials, Inc. |
| Selvol ® 502 and 205 PVA | Polyvinyl Alcohol (hydrolysis % = 87-89%), Sekisui Corporation |
| SLES-2 | Sulfochem ™ ES-2, Sodium Laureth Sulfate - 2 moles of ethoxylation (anionic surfactant), Lubrizol Advanced Materials, Inc. (27-28% active) |
| SLS | Sulfochem ™ Sodium Lauryl Sulfate (anionic surfactant), Lubrizol Advanced Materials, Inc. (30% active) |
| TBHP | t-butyl hydroperoxide (70%), Alfa Aesar |
| VA-086 | Azo VA-086 2,2'-Azobis[2-methyl-N-(2-hydroxyethyl)propionamide], Wako |

The following examples illustrate the technology disclosed herein. In all examples the amount of amphiphilic crosslinker reported is based on parts by wt. of the crosslinker per 100 parts by wt. of the monounsaturated monomers.

Example 1 (Comparative)

Monomer composition=HEMA/n-BA/EA/BEM/AX*(45/25/15/15/0.8)(wt. % total monomers) (*AX=0.8 wt. % based on total monounsaturated monomer wt.).

This example illustrates a polymer prepared in the presence of the protective colloid PVOH. An emulsion polymer was prepared as follows. A monomer premix was made by mixing 140 grams of D.I. D.I. water, 4 grams of E-Sperse RS-1618 amphiphilic crosslinker, 75 grams of (EA), 125 grams of (n-BA), 225 grams of (HEMA), 100 grams (BEM) from Solvay. Initiator A was prepared by dissolving 5 grams of Azo VA-086 in 40 grams of D.I. D.I. water. Initiator B was prepared by dissolving 2.5 grams of Azo VA-086 in 100 grams of D.I. water. A 3-liter reactor was charged with 770 grams of D.I. D.I. water, 6.67 grams of SLS and 10 grams of PVOH (Selvol 203), and then was heated to 87° C. under a nitrogen blanket with agitation. After holding the reactor contents at 87° C. for one hour, initiator A was then added to the reactor. After 3 minutes, the monomer premix was metered into the reaction vessel over a period of 120 minutes. About 1 minute after the start of monomer premix metering, Initiator B was metered into the reactor over a period of 150 minutes. The reaction temperature was maintained at 87° C. After completion of the initiator B feed, the temperature of the reactor contents was reduced to 85° C. for a period of 60 minutes. The reactor contents were then cooled to 49° C. A solution of 0.61 grams of 70% TBHP and 0.38 grams of SLS in 16.8 grams of D.I. D.I. water was added to the reactor. After 5 minutes, a solution of 0.59 grams of erythorbic acid in 16.8 grams of D.I. D.I. water was added to the reactor. The reactor contents were maintained at 49° C. After 30 minutes, a solution of 0.64 grams of 70% TBHP and 0.38 grams of SLS in 16.8 grams of D.I. D.I. water was added to the reactor. After 5 minutes, a solution of 0.59 grams of erythorbic acid in 16.8 grams of D.I. water was added to the reactor. The reactor contents were maintained at 49° C. for 30 minutes. The reactor contents were then cooled to room temperature (approximately 22° C.) and filtered through 100-micron mesh cloth. The pH of the resulting emulsion was adjusted to 4.5 with ammonium hydroxide. The polymer emulsion was diluted with 340 grams of D.I. D.I. water having a pH of 4.1, a solids content of 24.7 wt. %, a viscosity of 18 mPa·s, and an average particle size of 86 nm.

Example 2

Monomer composition=HEMA/n-BA/EA/BEM/AX*(45/25/15/15/0.8) (wt. % total monomers)) (*AX=0.8 wt. % based on total monounsaturated monomer wt.).

An emulsion polymer was prepared as follows. A monomer premix was prepared by mixing 200 grams of D.I. water, 4 grams of E-Sperse RS-1618 amphiphilic crosslinker, 28.41 grams of Glucamate™ VLT ethoxylated MEG triester amphiphilic additive, 75 grams of EA, 125 grams of n-BA, 225 grams of HEMA, 100 grams of BEM. Initiator A was prepared by dissolving 4 grams of Azo VA-086 in 40 grams of D.I. water. Initiator B was prepared by dissolving 0.75 grams of Azo VA-086 in 100 grams of D.I. water. A 3 liter reactor was charged with 770 grams of D.I. water, 6.67 grams of SLS and then the contents were heated to 90° C. under a nitrogen blanket with agitation. Initiator A was then added to the reactor. After 3 minutes, the monomer premix was metered into the reaction vessel over a period of 120 minutes. About 1 minute after the start of monomer premix feed, initiator B was metered into the reactor over a period of 150 minutes. The reaction temperature was then maintained at 87° C. After completion of the initiator B feed, the temperature of the reaction vessel contents were reduced to 85° C. for 60 minutes. The reactor was then cooled to 49° C. A solution of 0.61 grams of TBHP and 0.38 grams of SLS in 16.8 grams of D.I. water was added to the reactor. After 5 minutes, a solution of 0.59 grams of erythorbic acid in 16.8 grams of D.I. water was added to the reactor. The reactor contents were maintained at 49° C. After 30 minutes, a solution of 0.64 grams of TBHP and 0.38 grams of SLS in 16.8 grams of D.I. water was added to the reactor. After 5 minutes, a solution of 0.59 grams of erythorbic acid in 16.8 grams of D.I. water was added to the reactor. The reactor contents were maintained at 49° C. for 30 minutes. The reactor contents were then cooled to the room temperature (approximately 22° C.) and filtered through 100 micron mesh cloth. The resulting emulsion had a pH 3.1, a solids content of 29.1 wt. %, a viscosity of 125 mPa·s, and an average particle size of 82 nm.

Example 3

Monomer composition=HEMA/n-BA/EA/BEM/AX*(45/25/15/15/0.8) (wt. % total monomers) (*AX=0.8 wt. % based on total monounsaturated monomer wt.).

An emulsion polymer was prepared as follows. A monomer premix was prepared by mixing 225 grams of D.I. water, 3.33 grams of SLS, 4 grams of E-Sperse RS-1618 amphiphilic crosslinker, 47.62 grams of Glucamate™ LT ethoxylated MEG triester amphiphilic additive, 75 grams of EA, 125 grams of n-BA, 225 grams of HEMA, and 100 grams of BEM. Initiator A was prepared by dissolving 4 grams of Azo VA-086 in 40 grams of D.I. water. Initiator B was prepared by dissolving 0.75 grams of Azo VA-086 in 100 grams of D.I. water. A 3 liter reactor was charged with 770 grams of D.I. water, 6.67 grams of SLS and the contents were heated to 90° C. under a nitrogen blanket with agitation. Initiator A was then added to the reactor. After about 3 minutes, the monomer premix was metered into the reaction vessel over a period of 120 minutes. One minute after the start of monomer premix feed, initiator B was metered into the reactor over a period of 150 minutes. The reaction temperature was maintained at 87° C. during the feed. After completion of the initiator B feed, the temperature of the reaction vessel contents were reduced to 85° C. and this temperature maintained for 60 minutes. The reactor was then cooled to 49° C. A solution of 0.61 grams of TBHP and 0.38 grams of SLS in 16.8 grams of D.I. water was added to the reactor. After 5 minutes, a solution of 0.59 grams of erythorbic acid in 16.8 grams of D.I. water was added to the reactor. The reactor contents were maintained at 49° C. After 30 minutes, a solution of 0.64 grams of TBHP and 0.38 grams of SLS in 16.8 grams of D.I. water was added to the reactor. After 5 minutes, a solution of 0.59 grams of erythorbic acid in 16.8 grams of D.I. water was added to the reactor. The reactor contents were maintained at 49° C. for 30 minutes and. then cooled to room temperature (approximately 22° C.) and filtered through 100 micron mesh cloth. The polymer emulsion was diluted with D.I. water given a pH of 2.7, a solids content of 25.5 wt. %, a viscosity of 11 mPa·s, and an average particle size of 87 nm.

Example 4

Monomer composition=HEMA/n-BA/EA/BEM/AX*(45/25/15/15/0.8) (wt. % total monomers) (*AX=0.8 wt. % based on total monounsaturated monomer wt.).

An emulsion polymer was prepared as set forth in Example 3 except that 47.62 grams of the ethoxylated MEG triester (Glucamate™ LT thickener) was replaced by 20 grams of the ethoxylated MEG diester amphiphilic additive (Glucamate™ DOE 120 thickener). The polymer emulsion had a pH 2.7, a solids content of 25.9 wt. %, a viscosity of 15 mPa·s, and an average particle size of 86 nm.

Example 5

Monomer composition=HEMA/n-BA/EA/BEM/AX*(45/25/15/15/0.8) (wt. % total monomers) (*AX=0.8 wt. % based on total monounsaturated monomer wt.).

An emulsion polymer was prepared as set forth in Example 3 except that 47.62 grams of the Glucamate™ LT composition were replaced by 22.5 grams of poly(ethylene glycol-4000) dioleate amphiphilic additive and the SLS initially charged to the reactor was reduced to 2.5 grams from 6.67 grams. The polymer emulsion had a pH 3.6, a solids content of 26 wt. %, a viscosity 23 mPa·s, and an average particle size of 84 nm.

Example 6

Monomer composition=HEMA/n-BA/EA/BEM/AX*(45/25/15/15/0.8) (wt. % total monomers) (*AX=0.8 wt. % based on total monounsaturated monomer wt.).

An emulsion polymer was prepared the same manner as set forth in Example 3 except that 47.62 grams of the Glucamate™ LT composition were replaced by 22.5 grams of poly(ethylene glycol-1000) dioleate amphiphilic additive and the SLS initially charged to the reactor was reduced to 2.5 grams from 6.67 grams. The polymer emulsion had a pH 3.55, a solids content of 25.3 wt. %, a viscosity 20 mPa·s, and an average particle size of 84 nm.

Example 7

Monomer composition=HEMA/n-BA/EA/BEM/AX*(45/25/15/15/0.8) (wt. % total monomers) (*AX=0.8 wt. % based on total monounsaturated monomer wt.).

An emulsion polymer was prepared in the same manner as set forth in Example 3 except that 47.62 grams of Glucamate™ LT composition were replaced by 22.5 grams of poly(ethylene glycol-600 dioleate) amphiphilic additive, and the SLS initially charged to the reactor was reduced to 2.5 grams from 6.67 grams. The polymer emulsion had a of pH 3.6, a solids content of 24.8 wt. %, a viscosity of 18 mPa·s, and an average particle size of 84 nm.

Example 8

Monomer composition=HEMA/n-BA/EA/BEM/AX*(45/25/15/15/0.8) (wt. % total monomers) (*AX=0.8 wt. % based on total monounsaturated monomer wt.).

An emulsion polymer was prepared in the same manner as set forth in Example 3 except that 47.62 grams of Glucamate™ LT composition were replaced by 22.5 grams of poly(ethylene glycol-600 distearate) amphiphilic additive. The polymer emulsion had a pH of 3.5, a solids content of 24.8 wt. %, a viscosity of 16 mPa·s, and an average particle size of 84 nm.

Example 9

Monomer composition=HEMA/n-BA/EA/BEM/AX*(45/25/15/15/0.8) (wt. % total monomers) (*AX=0.8 wt. % based on total monounsaturated monomer wt.).

An emulsion polymer was prepared in the same manner as set forth in Example 3 except that 47.62 grams of the Glucamate™ LT component were replaced by 22.5 grams of a PPG-PEG-PPG block copolymer and the SLS initially charged to the reactor was reduced to 2.5 grams from 6.67 grams. The polymer emulsion had a pH of 3.4, a solids content of 25.15 wt. %, a viscosity of 17 mPa·s, and an average particle size of 82 nm.

Example 10 (Comparative)

Monomer composition=HEMA/n-BA/EA/BEM/AX*(45/25/15/15/0.8) (wt. % total monomers) (*AX=0.8 wt. % based on total monounsaturated monomer wt.).

An emulsion polymer was prepared in the same manner as set forth in Example 3 except that no amphiphilic additive component was incorporated into the monomer mix, and the SLS in the reactor was reduced to 4.17 grams from 6.67 grams. The polymer emulsion had a pH of 3.4, a solids content of 25.10 wt. %, a viscosity of 17 mPa·s, and particle an average size of 89 nm.

Example 11 (Comparative)

Monomer composition=HEMA/n-BA/EA/BEM/AX*(45/25/15/15/0.8) (wt. % total monomers) (*AX=0.8 wt. % based on total monounsaturated monomer wt.).

An emulsion polymer was prepared in the same manner as set forth in Example 3 except that no amphiphilic additive component was utilized in the monomer mix and the SLS initially charged to the reactor was reduced to 2.5 grams from 6.67 grams. The polymer emulsion had a pH of 3.4, a solids content of 25.10 wt. %, a viscosity of 20 mPa·s, and an average particle size of 99.4 nm.

Example 12 (Comparative)

Monomer composition=HEMA/n-BA/EA/BEM/AX*(45/25/15/15/0.8) (wt. % total monomers) (*AX=0.8 wt. % based on total monounsaturated monomer wt.).

An emulsion polymer was prepared the same manner as set forth in Example 4, except that 20 grams of the ethoxylated MEG diester amphiphilic additive (Glucamate™ DOE 120 thickener) was charged into the reactor instead of mixing with the monomer premix. The final water dilution step was also skipped. The polymer latex had a pH of 3.3, a solids content of 27.5 wt. %, a viscosity of 11 mPa·s, and particle size 137 nm.

Example 13

The polymer of Comparative Example 1 was formulated with the components set forth in Table 1.

TABLE 1

| Part | Ingredients | Active % |
|---|---|---|
| A | D.I. Water | q.s. to 100 |
|   | Polymer of Example 1 | 2.5 |
| B | SLES-2 | 9 |
|   | CAPB | 3 |
| C | PEG-7 Glyceryl Cocoate | 1 |
|   | Fragrance Oil | 1 |
|   | PEG-40 Hydrogenated Castor Oil | 0.6 |
| D | Sodium Benzoate (20% aqueous) | 0.5 |
| E | Citric acid (50% aqueous) | pH to 4.0 to 5.0 |

1) The Part A component was prepared by adding the amphiphilic polymer to D.I. water followed by mixing with an overhead mixer at 200 rpm until homogeneous.
2) The Part B components were added to Part A and mixed via an overhead mixer at 350 rpm for 5 minutes or until the Part AB mixture became transparent.

3) In a separate vessel, the Part C ingredients were mixed until homogeneous and the mixture was added drop-wise to the PART AB mixture, whereupon the mixture immediately became translucent. The PART ABC mixture was mixed with an overhead mixer at 350 rpm for 5 minutes or until the fragrance was homogeneously dispersed and the mixture turned to the transparent state (about 5 minutes).

4) Part D was added to the ABC mixture and stirred until a homogeneous ABCD mixture was obtained.

5) Equal aliquots (99.4 g) of the ABCD mixture were transferred to separate vessels and the Part E component (citric acid solution) was added to each of the individual samples to adjust the pH to a desired value. Each sample was then mixed at 350 rpm with an overhead mixer for about 30 minutes.

6) Each sample was then equilibrated to room temperature (approximately 22° C.) for 24 hours and was centrifuged to remove air bubbles and any undissolved solids before testing for physical properties.

Optical Clarity

Samples of the formulation containing the comparative polymer of Example 1 and pH adjusted to values of 4.1, 4.5 and 4.9 were tested for clarity as set forth in the light transmittance methodology set forth above. The result for the light transmittance test for each formulation versus pH is plotted in FIG. 1.

Structural coloration, common in nature, is the creation of color by microscopically structured surfaces which interfere with the visible light spectrum. As shown in FIG. 1, the clarity of the surfactant composition containing the polymer of Comparative Example 1 (prepared with polyvinyl alcohol) is 60% T at a wavelength of 400 nm which is indicative of a translucent appearance. Moreover, the % T value for the tested formulations near the blue light region (wavelength of 450 to 495 nm) is affected by a bluish structural color, where a sharp transition near the wavelength of 475 nm was observed. Therefore, the clarity at lower wavelengths for a formulation containing the polymer of Comparative Example 1 was not good.

Example 14

To quantify the intensity of the structural color of surfactant formulation containing a polymer of the present technology, the polymer of Example 2 was formulated with the same components and methodology as set forth in Example 13. The diffuse reflection properties of the sample was measured by the methodology described in the Diffuse Reflection Test described above. The polymer of Comparative Example 1 was identically formulated and tested.

Figure 2:
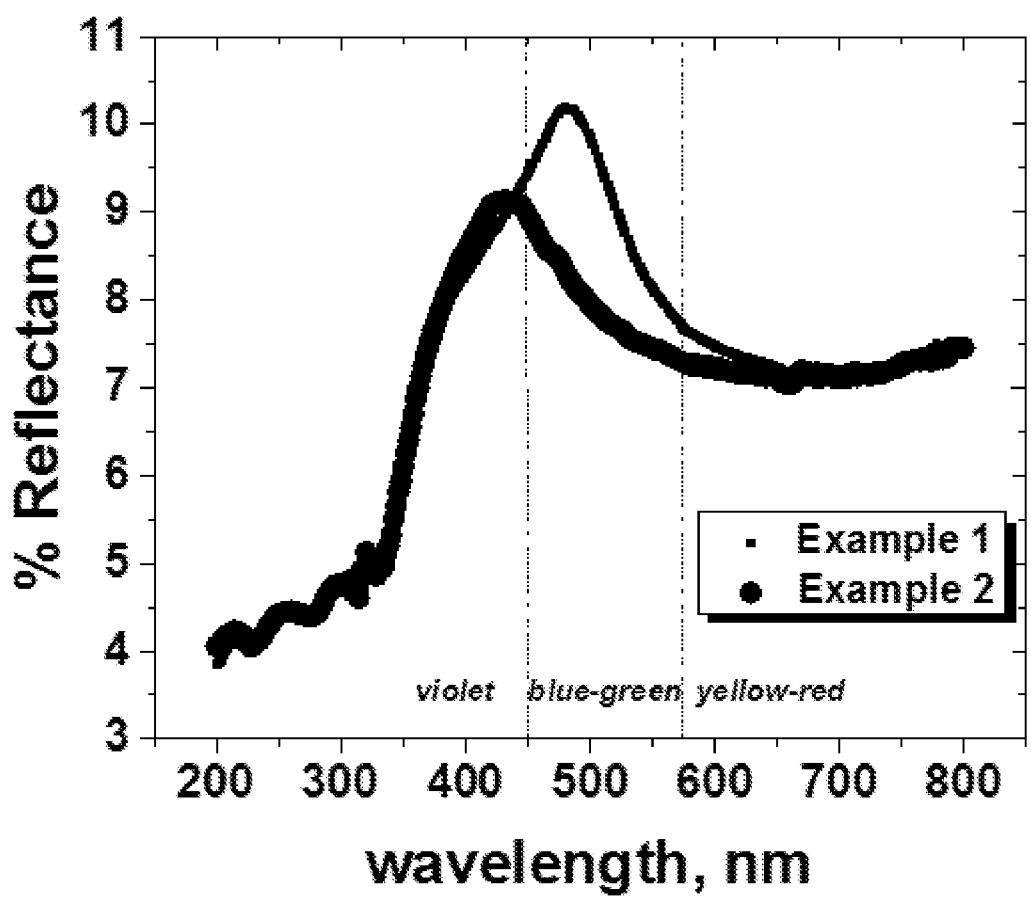
FIG. 2 is a plot that compares the diffuse reflectance (% reflectance versus wavelength of visible light) of surfactant formulations containing the polymers of Comparative Example 1 and Illustrative Example 2.

As set forth in FIG. 2, the formulation containing the polymer of Comparative Example 1 exhibited a reflection peak in the blue wavelength region and the reflection intensity was much larger than the formulation containing the polymer of Example 2.

Example 15

Figure 3:
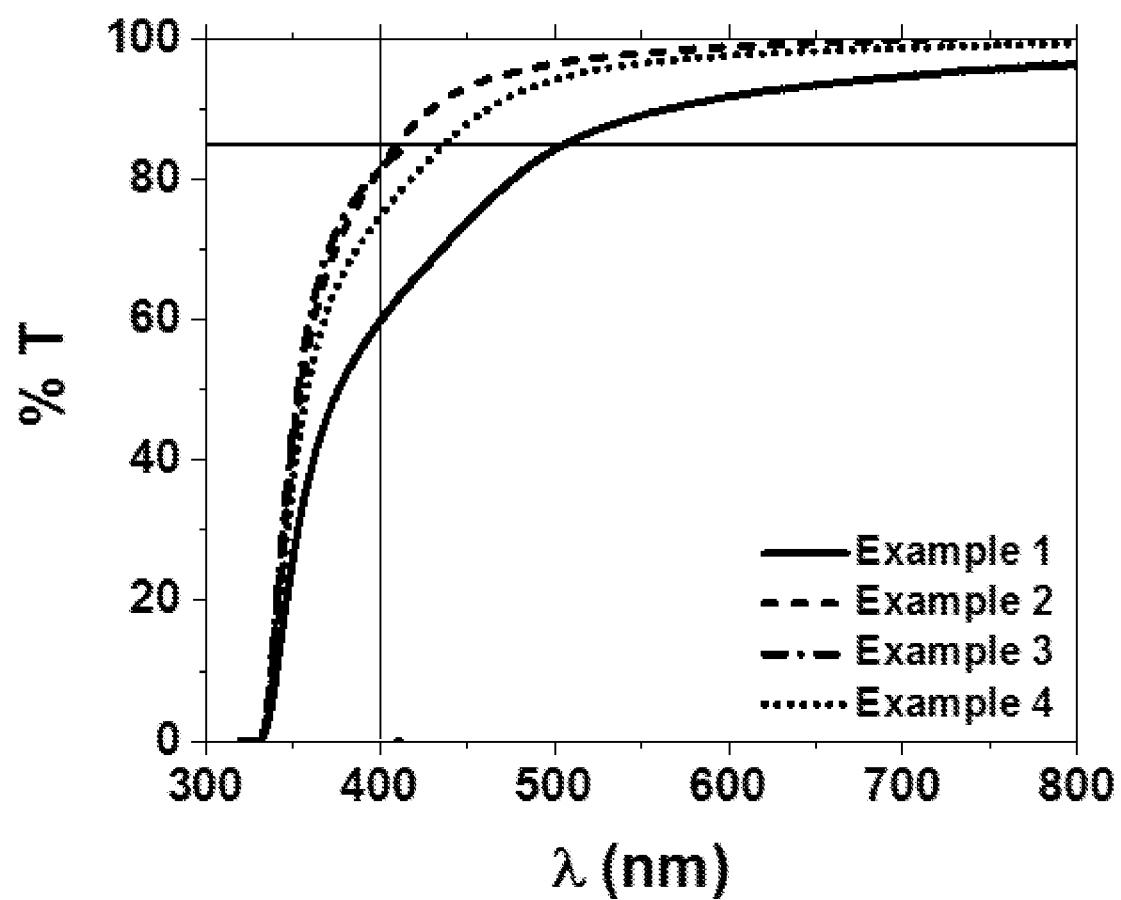
FIG. 3 is a plot comparing the light transmittance curves (% T versus the wavelength of visible light) for surfactant formulations containing the polymers of Comparative Example 1 and Illustrative Examples 2 to 4.

The polymers of Comparative Example 1 and Examples 2 to 4 were formulated utilizing the same components and procedures as set forth in Example 12. The rheology and clarity properties (turbidity and % T) of each of the polymer formulations were measured as set forth in the methodology described above. The rheology and turbidity results are reported in Table 2 and clarity values (% T) are plotted in FIG. 3.

TABLE 2

| Polymer Ex. No. | Amphiphilic Additive | Steric Stabilizer | Viscosity (mPa · s) | Yield stress (Pa @ 1 rad/s) | Turbidity (NTU) | % T (@ 400 nm) |
|---|---|---|---|---|---|---|
| 1 | — | PVOH | 9,000 | 6.4 | 18.8 | 59.8 |
| 2 | EMegE[2] | — | 13,260 | 8 | 9.6 | 80.0 |
| 3 | EMegE[2] | — | 13,540 | 5.5 | 9.3 | 81.5 |
| 4 | EMegE[2] | — | 10,320 | 4.7 | 9.8 | 79.3 |

[1]polyvinyl alcohol
[2]ethoxylated MEG ester

While the rheological properties (viscosity and yield stress) of surfactant formulations containing the polymer of Comparative Example 1 (prepared in the presence of a PVOH steric stabilizer) and the polymers of Examples 2 to 4 (prepared in the presence of polymeric modifiers of the present technology) are similar, the turbidity and clarity properties are significantly improved when utilizing the polymers of the present technology.

Example 16

Surfactant compositions containing yield stress enhancing polymers were formulated with the components set forth in Table 3. The rheology (viscosity and yield stress) and clarity properties (turbidity) of each of the polymer formulations were measured as set forth in the methodology described above. The rheology and turbidity results are reported in Table 4.

TABLE 3

| Part | Ingredients | Active wt. % |
|---|---|---|
| A | D.I. Water | q.s. to 100 |
|   | Polymer Example No. (see Table 4) | 2.5 |
| B | SLES-2 | 10 |
|   | CAPB | 1.7 |
| C | PEG-7 Glyceryl Cocoate | 0.5 |
|   | Fragrance | 1 |
|   | Polyquarternium-7 | 0.11 |
| D | Sodium Benzoate (20% aqueous solution) | 0.5 |
| E | Citric acid (50% aqueous solution) | pH to 4.5 to 5.0 |

1) The Part A component was prepared by adding the amphiphilic polymer to D.I. water followed by mixing with an overhead mixer at 200 rpm until homogeneous.
2) The Part B components were added to Part A and mixed via an overhead mixer at 350 rpm for 5 minutes or until the Part AB mixture became transparent.
3) The Part C components were individually added in the order listed (top to bottom) by drop-wise addition to the PART AB mixture. Each component was homogeneously mixed before the next component was added. After all Part C components were added, the ABC mixture was agitated with an overhead mixer at 350 rpm for 5 minutes.

4) Part D was added to the ABC mixture and stirred until a homogeneous ABCD mixture was obtained.

5) Equal aliquots (99.4 g) of the ABCD mixture were transferred to separate vessels and component E (citric acid solution) was added to each of the individual sample to adjust the pH to a desired value. Each sample was then mixed at 350 rpm with an overhead mixer for about 30 minutes.

6) Each sample was then equilibrated to room temperature (approximately 22° C.) for 24 hours and was centrifuged to remove air bubbles and any undissolved solids before testing for physical properties.

TABLE 4

| Polymer Ex. No. | Amphiphilic Additive | Steric Stabilizer | Viscosity (mPa·s) | Turbidity (NTU) | Yield Stress (Pa @ 1 rad/s) | Bead Suspension 50° C. @ 6 weeks |
|---|---|---|---|---|---|---|
| 1[1] | — | PVOH | 13,300 | 25.3 | 11.2 | Pass |
| 2 | EMegE | — | 16,800 | 12.8 | 9.8 | Pass |
| 3 | EMegE | — | 14,350 | 14.2 | 10.7 | Pass |
| 4 | EMegE | — | 18,550 | 16.1 | 12.4 | Pass |
| 5 | Poly(ethylene glycol-4000) dioleate | — | 16,020 | 16.5 | 8.9 | Pass |
| 6 | Poly(ethylene glycol-1000) dioleate | — | 12,140 | 13.5 | 4.3 | Pass |
| 7 | Poly(ethylene glycol-4000) dioleate | — | 11,780 | 15.6 | 2.6 | Pass (NTL 2100 beads) |
| 8 | Poly(ethylene glycol-600) distearate | — | 12,350 | 14.9 | 5.1 | Pass |
| 9 | Pluronics™ 10R5 PPG-PEG-PPG Block Copolymer | — | 7,320 | 16.5 | 5.8 | Pass |
| 10[1] | — | — | 17,140 | 23.6 | 11.0 | Pass |
| 11[1] | — | — | 16,150 | 40.6 | 14.8 | Pass |

[1]Comparative

The surfactant formulations containing polymers prepared with PVOH steric stabilizer or no steric stabilizer and no amphiphilic polymerization additive had similar rheological properties to surfactant compositions containing polymers prepared with amphiphilic polymerization additives, but exhibited inferior turbidity properties.

Example 17

To determine if the post addition of an amphiphilic additive of the present technology imparts improvements in the turbidity values of surfactant compositions containing a crosslinked amphiphilic polymer that was not prepared in the presence an amphiphilic additive of the present technology, an equivalent amount of the amphiphilic additive used to prepare the polymer of Example 3 was post added to the surfactant formulations for Polymer Ex. Nos. 10 and 11 in Table 4 of Example 16. The rheological properties and turbidity values are reported in Table 5.

TABLE 5

| Polymer No. | Amphiphilic Additive Pre-Addition | Amphiphilic Additive Post Addition | Viscosity (mPa·s) | Turbidity (NTU) | Yield Stress (Pa @ 1 rad/s) | Suspension 50° C. @ 6 weeks |
|---|---|---|---|---|---|---|
| 3 (Ex. 16) | 0.11 | 0 | 14,350 | 14.2 | 10.7 | Pass |
| 10 (Ex. 16) | 0 | 0 | 17,140 | 23.6 | 11.0 | Pass |
| 11 (Ex. 16) | 0 | 0 | 16,150 | 40.6 | 14.8 | Pass |

TABLE 5-continued

| Polymer No. | Amphiphilic Additive Pre-Addition | Amphiphilic Additive Post Addition | Viscosity (mPa · s) | Turbidity (NTU) | Yield Stress (Pa @ 1 rad/s) | Suspension 50° C. @ 6 weeks |
|---|---|---|---|---|---|---|
| 10 (Ex. 16) | 0 | 0.11 | 21,650 | 23.2 | 12.6 | Pass |
| 11 (Ex. 16) | 0 | 0.11 | 21,350 | 40.6 | 16.1 | Pass |

The results indicate that surfactant formulations containing a polymer that was prepared by polymerizing a monomer mixture containing an amphiphilic additive (pre-addition) improves turbidity values, while surfactant formulations containing a polymer prepared by polymerizing a monomer mixture devoid of an amphiphilic additive but where an equivalent amount of amphiphilic additive used in the pre-addition process is post added to the surfactant containing polymer formulation do not improve turbidity values.

Example 18

The polymer of Comparative Example 12 was formulated with the ingredients, amounts and procedures set forth in Table 3 of Example 16. The physical properties of the formulation are set forth in Table 6.

TABLE 6

| Polymer Ex. No. | Amphiphilic Additive | Viscosity (mPa · s) | Turbidity (NTU) | Yield Stress (Pa @ 1 rad/s) | Bead Suspension 40° C. @ 12 weeks | Bead Suspension 45° C. @ 12 weeks | Bead Suspension 50° C. @ 6 weeks |
|---|---|---|---|---|---|---|---|
| 12[1] | In Reactor | 24,660 | 78.6 | 11.8 | Fail | Fail | Fail |

[1]comparative

The results indicate that surfactant formulations containing a polymer that was prepared by polymerizing a monomer mixture having the amphiphilic additive placed into the polymerization medium instead of being mixed into the polymerizable monomer composition are significantly more turbid than surfactant compositions containing the polymer of the present technology prepared by polymerizing a monomer mixture where the amphiphilic additive is mixed with the monomer mixture before polymerization. Surfactant compositions containing the comparative polymer also fail the bead suspension test after 12 weeks at 40° C. and 6 weeks at 50° C.

While certain representative embodiments and details have been shown for the purpose of illustrating the subject technology, it will be apparent to those skilled in this art that various changes and modifications can be made therein without departing from the scope of the subject disclosed technology. In this regard, the scope of the disclosed technology is to be limited only by the following claims.

What is claimed is:

1. A crosslinked nonionic amphiphilic emulsion polymer prepared by polymerizing a monounsaturated monomer composition comprising:
   a) from about 20 to about 50 wt. % of hydroxyethyl methacrylate;
   b) from about 10 to about 30 wt. % ethyl acrylate;
   c) from about 10 to about 30 wt. % butyl acrylate;
   d) from about 1 to about 15 wt. % of at least one associative and/or semi-hydrophobic monomer (wherein all monomer weight percentages are based on the weight of the total monounsaturated monomers);
   e) from about 0.01 to about 5 parts by wt. % of at least one crosslinker, based on 100 parts by wt. of the monounsaturated monomers utilized to prepare the polymer, selected from an amphiphilic crosslinking agent; and
   f) from about 1 to about 15 parts by wt., based on 100 parts by wt. of the monounsaturated monomers utilized to prepare the polymer, of a polyethyoxylated alkyl glucoside ester selected from the formula:

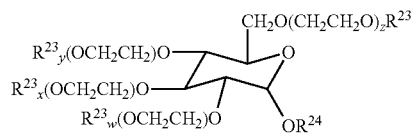

wherein $R^{23}$ is independently selected from H and a saturated and unsaturated $C_{10}$-$C_{22}$ acyl group; $R^{24}$ is selected from a $C_1$-$C_{10}$ alkyl group; and the sum of w+x+y+z ranges from about 60 to about 150; subject to the proviso that at no more than two of $R^{23}$ can be H at the same time.

2. The emulsion polymer of claim 1 wherein in said polyethyoxylated alkyl glucoside ester $R_{24}$ is methyl and the sum of w+x+y+z is 120.

3. The emulsion polymer of claim 1 wherein the amount of amphiphilic additive present in the polymerizable monounsaturated monomer composition ranges from about 1 to about 15 parts by wt., based on the 100 parts by wt. of the total monounsaturated monomers.

4. The emulsion polymer of claim 1 wherein said associative monomer is represented by formula:

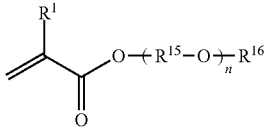

wherein $R^{14}$ is hydrogen or methyl; $R^{15}$ is a divalent alkylene moiety independently selected from the group consisting of $C_2H_4$, $C_3H_6$, and $C_4H_8$, and n represents an integer ranging from about 10 to about 60, ($R^{15}$—O) can be arranged in a random or a block configuration; $R^{16}$ is a substituted or unsubstituted alkyl selected from the group consisting of a $C_8$-$C_{30}$ linear alkyl, a $C_8$-$C_{30}$ branched alkyl, a $C_8$-$C_{30}$ carbocyclic alkyl, a $C_2$-$C_{30}$ alkyl-substituted phenyl, an araalkyl substituted phenyl, and an aryl-substituted $C_2$-$C_{30}$ alkyl, wherein the $R^{16}$ alkyl group, aryl group, phenyl group optionally comprises one or more substituents selected from the group consisting of a hydroxyl group, an alkoxyl group, benzyl group styryl group, and a halogen group.

5. The emulsion polymer of claim 4 wherein said associative monomer in said monounsaturated monomer composition is selected from the group consisting of lauryl polyethoxylated (meth)acrylate, cetyl polyethoxylated (meth)acrylate, cetearyl polyethoxylated (meth)acrylate, stearyl polyethoxylated (meth)acrylate, arachidyl polyethoxylated (meth)acrylate, behenyl polyethoxylated (meth)acrylate, cerotyl polyethoxylated (meth)acrylate, montanyl polyethoxylated (meth)acrylate, and melissyl polyethoxylated (meth)acrylate, where the polyethoxylated portion of the monomer contains about 2 to about 50 ethylene oxide units.

6. The emulsion polymer of claim 1 wherein said semi-hydrophobic monomer is selected from at least one monomer represented the following formulas:

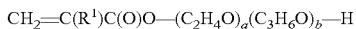

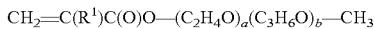

wherein $R^1$ is hydrogen or methyl, and "a" is an integer ranging from 0 or 2 to about 120 and "b" is an integer ranging from about 0 or 2 to about 120, subject to the proviso that "a" and "b" cannot be 0 at the same time.

7. The emulsion polymer of claim 6 wherein b is 0.

8. The emulsion polymer of claim 1 wherein said amphiphilic crosslinking agent is a compound of formula:

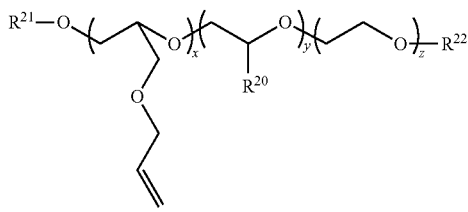

where:
$R^{21}$ is a $C_{10-24}$ alkyl, alkaryl, alkenyl, or cycloalkyl;
$R^{20}$ is $CH_3$, $CH_2CH_3$, $C_6H_5$, or $C_{14}H_{29}$;

$R^{22}$ is H or $Z^- M^+$
$Z^-$ is $SO_3^-$, or $PO_3^{2-}$;
$M^+$ is $Na^+$, $K^+$, $NH_4^+$, or an alkanolamine;
x is 2-10;
y is 0-200; and
z is 4-200.

9. The emulsion polymer of claim 8 wherein the amphiphilic crosslinking agent is a compound of formula:

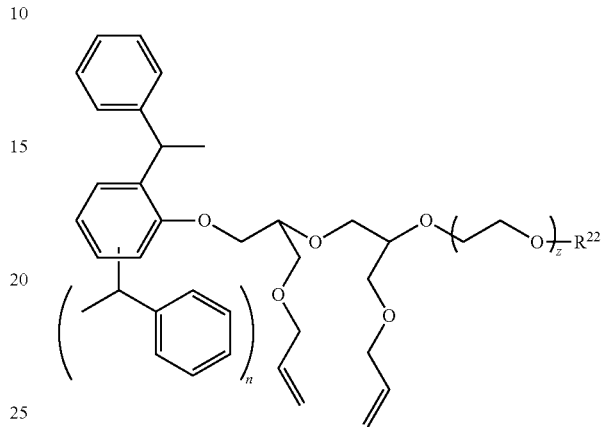

where:
n is 1 or 2;
z is 4 to 40; and
$R^{22}$ is H, $SO_3^-M^+$ or $PO_3^{2-}M^+$, and M is selected from $Na^+$, $K^+$, $NH_4^+$ or an alkanolamine.

10. The emulsion polymer of claim 1 wherein said monounsaturated monomer composition further comprises a conventional crosslinking agent which is present in an amount sufficient to be incorporated into said polymer from about 0.01 to about 1 parts by wt., based on 100 parts by weight of the monounsaturated monomers utilized to prepare the polymer.

11. The emulsion polymer of claim 10 wherein said monounsaturated monomer mixture comprises a conventional crosslinking agent which is present in an amount sufficient to be incorporated into said polymer from about 0.01 to about 0.3 parts by wt., based on 100 parts by wt. of the monounsaturated monomers utilized to prepare the polymer.

12. The emulsion polymer of claim 10 wherein the conventional crosslinking agent is selected from the group consisting of polyallyl ethers of trimethylolpropane, polyallyl ethers of pentaerythritol, polyallyl ethers of sucrose, and mixtures thereof.

13. The emulsion polymer of claim 12 wherein the conventional crosslinking agent is selected from the group consisting of pentaerythritol diallyl ether, pentaerythritol triallyl ether, pentaerythritol tetraallyl ether, and mixtures thereof.

14. The emulsion polymer of claim 1 wherein said monounsaturated monomer composition further comprises from about 0 or 1 to about 15 parts by wt., based on 100 parts by wt. of the polymerizable monounsaturated monomers in the mixture, of a $C_6$ to $C_{22}$ alkyl (meth)acrylate.

15. The emulsion polymer of claim 14 wherein said $C_6$ to $C_{22}$ alkyl (meth)acrylate is selected from the group consisting of hexyl (meth)acrylate, heptyl (meth)acrylate, octyl (meth)acrylate, 2-ethylhexyl (meth)acrylate, decyl (meth)acrylate, isodecyl (meth)acrylate, lauryl (meth)acrylate, tetradecyl (meth)acrylate, hexadecyl (meth)acrylate, stearyl (meth)acrylate, behenyl (meth)acrylate, and mixtures thereof.

16. The emulsion polymer of claim 1 wherein said monounsaturated monomer composition is polymerized in the absence of a protective colloid.

17. The emulsion polymer of claim 1 wherein said monounsaturated monomer composition is polymerized in the absence of poly(vinyl alcohol) and poly(vinyl acetate).

18. The emulsion polymer of claim 1 wherein said monounsaturated monomer composition further comprises 1 to 6 wt. % of a residual ionic or ionizable monomer.

19. The emulsion polymer of claim 1 wherein said monounsaturated monomer composition further comprises a residual amount of methacrylic acid.

20. A yield stress fluid composition comprising:
 (A) water;
 (B) about 0.1 to about 5 wt. % of at least one crosslinked nonionic amphiphilic emulsion polymer prepared according to claim 1; and
 (C) from about 5 to about 50 wt. % based on the total weight of the yield stress fluid of at least one surfactant.

21. The composition of claim 20 wherein the concentration of said polymer ranges from about 0.5 to about 3 wt. %.

22. The composition of claim 20 wherein the at least one surfactant is selected from anionic, cationic, amphoteric, nonionic, or mixtures thereof.

23. The composition of claim 22 wherein the ratio of the anionic surfactant to the amphoteric surfactant, active material, is 10:1 to about 2:1.

24. The composition of claim 20 wherein the at least one surfactant is an anionic surfactant.

25. The composition of claim 20 wherein the at least one surfactant is selected from the group consisting of an anionic surfactant and an amphoteric surfactant.

26. The composition of claim 25 wherein the at least one anionic surfactant is selected from sodium dodecyl sulfate, sodium lauryl sulfate, sodium laureth sulfate, or mixtures thereof.

27. The composition of claim 25 wherein the at least one amphoteric surfactant is cocamidopropyl betaine.

28. The composition of claim 20 wherein a concentration of the at least one surfactant is from 5 to less than 25 wt. %, based on the weight of the yield stress fluid.

29. The composition of claim 20 wherein a concentration of the at least one surfactant ranges from about 6 to about 20 wt. %, active material, based on the weight of the total composition.

30. A method for improving the clarity of a surfactant containing yield stress fluid by incorporating the polymer of claim 1 therein.

* * * * *